United States Patent
Morita et al.

(10) Patent No.: US 8,391,572 B2
(45) Date of Patent: Mar. 5, 2013

(54) APPARATUS FOR AIDING PHOTOGRAPHING OF MEDICAL IMAGE AND COMPUTER PROGRAM PRODUCT FOR THE SAME

(75) Inventors: Junya Morita, Kanagawa-ken (JP); Masahiko Yamada, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 822 days.

(21) Appl. No.: 12/461,491

(22) Filed: Aug. 13, 2009

(65) Prior Publication Data
US 2010/0054557 A1    Mar. 4, 2010

(30) Foreign Application Priority Data
Aug. 27, 2008    (JP) .................. 2008-218223

(51) Int. Cl.
*G06K 9/00*    (2006.01)
(52) U.S. Cl. ...................................... 382/128
(58) Field of Classification Search .............. 382/128, 382/131, 132; 250/370.08–370.1; 378/20, 378/37, 177
See application file for complete search history.

(56) References Cited

U.S. PATENT DOCUMENTS

| | | | | |
|---|---|---|---|---|
| 5,334,851 A * | 8/1994 | Good et al. | | 250/582 |
| 6,075,879 A * | 6/2000 | Roehrig et al. | | 382/132 |
| 6,431,440 B1 * | 8/2002 | Tsuchino | | 235/380 |
| 7,809,102 B2 * | 10/2010 | Brada et al. | | 378/20 |
| 7,865,002 B2 * | 1/2011 | Basilico et al. | | 382/128 |
| 2002/0060302 A1 * | 5/2002 | Aonuma | | 250/583 |
| 2005/0023495 A1 * | 2/2005 | Tamakoshi et al. | | 250/586 |
| 2005/0180544 A1 * | 8/2005 | Sauer et al. | | 378/195 |
| 2006/0002633 A1 * | 1/2006 | Takeo | | 382/294 |
| 2006/0203958 A1 * | 9/2006 | Nagamine et al. | | 378/20 |
| 2007/0053492 A1 * | 3/2007 | Kidani et al. | | 378/65 |
| 2007/0086641 A1 | 4/2007 | Nakamura | | |
| 2007/0248210 A1 * | 10/2007 | Selse et al. | | 378/37 |
| 2007/0269017 A1 * | 11/2007 | Umeki et al. | | 378/165 |
| 2008/0002871 A1 * | 1/2008 | Gunzert-Marx et al. | | 382/132 |

FOREIGN PATENT DOCUMENTS

| | | |
|---|---|---|
| JP | 2001-034765 A | 2/2001 |
| JP | 2007-105264 A | 4/2007 |

OTHER PUBLICATIONS

Tokiko Endo; Diagnostic Imaging which I want a Radiation Technologist to Know: Breast; Mar. 15, 2006; p. 18; 1st edition; Sin'ichi Koyashiki, Iryou Kagaku Co. Ltd.; Japan.

* cited by examiner

*Primary Examiner* — Claire X Wang
*Assistant Examiner* — Shervin Nakhjavan
(74) *Attorney, Agent, or Firm* — Jean C. Edwards, Esq.; Edwards Neils PLLC

(57) ABSTRACT

An apparatus for aiding photographing of a medical image, including an image acquiring device for acquiring a medical image obtained by radiation-photographing of a part including a diagnosis target region of a test subject; a positioning evaluating device for analyzing the acquired medical image and evaluating positioning of the test subject at a time of the radiation-photographing; a positioning cautions creating device for creating positioning cautions based on an evaluation result by the positioning evaluating device; and a positioning cautions presenting device for presenting the positioning cautions created by the positioning cautions creating device.

35 Claims, 16 Drawing Sheets

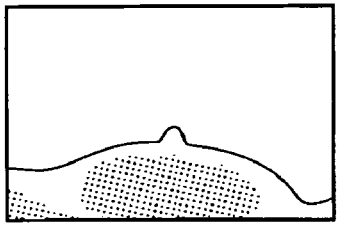
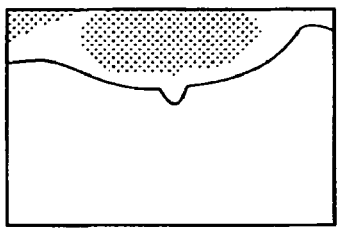

FIG.5A
BREAST IMAGE

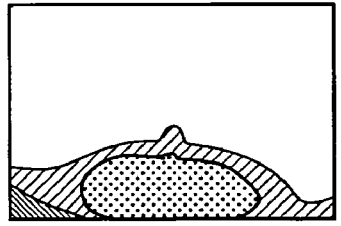
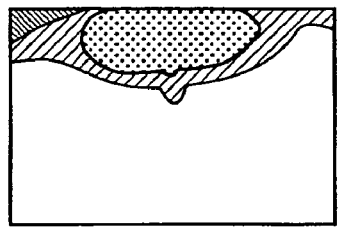

FIG.5B
EXTRACT ANATOMICAL STRUCTURES (BREAST, MAMMARY GLAND, GREATER PECTORAL MUSCLE, NIPPLE)

FIG.5C
EVALUATION OF EACH ITEM OF POSITIONING (QUANTIFICATION)

| EVALUATION OF LATERAL SYMMETRY | EVALUATION OF LATERAL ORIENTATION OF NIPPLE | EVALUATION OF GREATER PECTORAL MUSCLE | EVALUATION OF SPACE BEHIND MAMMARY GLAND | EVALUATION OF REGION UNDER BREAST | EVALUATION OF EXTENSION OF MAMMARY GLAND |

FIG.10

| POSITIONING EVALUATION ITEM | | EVALUATION POINT |
|---|---|---|
| LATERAL SYMMETRY | | 4 POINTS |
| LATERAL ORIENTATION OF NIPPLE | | 4 POINTS |
| GREATER PECTORAL MUSCLE | POSITION OF LOWER END PORTION | 2 POINTS |
| | SHAPE | 1 POINT |
| | AREA | 1 POINT |
| SPACE BEHIND MAMMARY GLAND | | 4 POINTS |
| PART UNDER BREAST | | 4 POINTS |
| EXTENSION OF MAMMARY GLAND | | 4 POINTS |

APPARATUS FOR AIDING PHOTOGRAPHING OF MEDICAL IMAGE AND COMPUTER PROGRAM PRODUCT FOR THE SAME

CROSS-REFERENCE TO RELATED APPLICATIONS

The present application claims priority from Japanese Patent Application No. 2008-218223, filed Aug. 27, 2008, the contents of which are herein incorporated by reference in their entirety.

BACKGROUND OF THE INVENTION

1. Field of the Invention

The present invention relates to an apparatus for aiding photographing of a medical image and a computer program product for the same, and particularly relates to the art of aiding positioning of a test subject at a time of photographing.

2. Description of the Related Art

In photographing of a medical image, it is important to perform suitable positioning (positioning the body posture of a test subject) under suitable photographing conditions in order to obtain a useful image for diagnosis.

There is conventionally proposed an apparatus which aids determination of which is a necessary part for photographing or under what photographing conditions, photographing should be performed by displaying the past image of a same patient and its accessory information (measurement processing result and the detection result of an abnormal shadow) at a time of photographing (Japanese Patent Application Laid-Open No. 2001-34765).

Further, there is proposed an apparatus which extracts an anatomical structure from the photographed medical image, determines whether the image is a suitable image for performing diagnosis of a diagnostic region photographed in the medical image on the basis of the extracted structure, and displays the determination result (Japanese Patent Application Laid-Open No. 2007-105264).

SUMMARY OF THE INVENTION

However, in the case of the apparatus described in Japanese Patent Application Laid-Open No. 2001-34765, a photographer needs to determine what positioning the photographer should perform at the time of photographing while checking the past image and the detection result of the abnormal shadow, and there arises the problem of being troublesome, and there also arises the problem that small points to be improved of positioning are likely to be missed.

Further, in the case of the apparatus described in Japanese Patent Application Laid-Open No. 2007-105264, the apparatus determines whether or not the photographed image is an image suitable for performing diagnosis, and the determination result (warning and numerical value) is displayed, but the photographer needs to determine what positioning the photographer should perform at a time of photographing on the basis of the determination result, and there is the problem of being troublesome.

In the diagnostic imaging of breast cancer by mammography, X-ray absorption difference between a lesion and normal tissue is extremely small, and diagnosis of a very small lesion is required. Therefore, an image with high quality is required. Among the factors which give influence on the quality of the image, the influence of the photographing technique is especially large, and failure in positioning and compression of the breast can be a factor of missing a deep lesion and a very small light lesion.

Meanwhile, since the sizes and shapes of breasts, mammary gland density and physiques of the test subjects vary widely, and mammography is particular kind of photographing which is performed by sufficiently widening mammary glands and compressing them, there is the problem that mammography is very difficult.

Specifically, mammography has the following differences from ordinary photography of a chest, bone and the like, and difficulty in photographing.

<Difference Between Mammography and Ordinary Photography>

(1) Compression Photographing

In mammography, the structure (tumor) with a small X-ray absorption difference which the other regions do not have needs to be visualized. Therefore, under the condition that the mammary glands are compressed so that the mammary glands completely extended and the mammary glands do not overlap one another, photographing is performed so that whether the photographed tissue is a mammary or a tumor can be determined.

(2) Photographing of Soft Tissue

In order to visualize the entire mammary glands, an operation of sufficiently moving a movable tissue to a fixed tissue side is required. By only photographing a breast by being sandwiched with compression plates, there is a problem that a defective region occurs.

<Difficulty of Mammography>

Since mammography has particularity as described above, mammography has so many points to which attention should be given in order to (a) perform photographing by sufficiently extending mammary glands and to (b) prevent a defective region from occurring as much as possible, as well as the points of positioning in general photography (standing position and orientation of the test subject, and photographing range).

Further, the breasts are said to have the largest individual difference among human organs, therefore, positioning needs to be considered in accordance with not only the physique of the test subject, but also the individual difference such as the size, shape and mammary gland percentage content of the breast.

From the above described reasons, mammography is very difficult, and requires a photographing technique at a high degree.

The present invention is made in view of the above circumstances, and has an object to provide an apparatus for aiding photographing of a medical image and a computer program product for the same by which a photographer can efficiently grasp points to be improved of positioning and by which suitable positioning for each of a test subject and improvement in a photographic technique of a photographer can be aided.

In order to attain the above-described object, an apparatus for aiding photographing of a medical image according to the first aspect of the present invention includes an image acquiring device for acquiring a medical image obtained by radiation-photographing of a part including a diagnosis target region of a test subject; a positioning evaluating device for analyzing the acquired medical image and evaluating positioning of the test subject at a time of the radiation-photographing; a positioning cautions creating device for creating positioning cautions based on an evaluation result by the positioning evaluating device; and a positioning cautions presenting device for presenting the positioning cautions created by the positioning cautions creating device.

The photographer can receive presentation of the positioning cautions, which are automatically created from the evaluation result obtained by analysis of the medical image, with respect to the medical image (including the medical image after photographing) of the past. Thereby, the photographer can easily grasp a point to be improved of positioning at a time of photographing the next medical image.

The apparatus for aiding photographing of the medical image according to the second aspect of the present invention is, in the apparatus according to the first aspect, the apparatus wherein the positioning evaluating device makes evaluation for each of a plurality of items of the positioning, and outputs an evaluation result of each of the items. For example, when mammography is performed as the medical image, positioning needs to be performed so that the entire mammary gland tissue where a lesion occurs is properly compressed and extended to be visualized, it is known that there are a plurality of evaluation items of the positioning, and the positioning evaluating device makes evaluation for each of the plurality of items of positioning.

The apparatus for aiding photographing of the medical image according to the third aspect of the present invention, in the apparatus according to the first or second aspect, further includes a positioning cautions storing device for storing test subject identification information for identifying the test subject corresponding to the medical image and positioning cautions created for the medical image by the positioning cautions creating device by linking the test subject identification information and the positioning cautions with each other; and a test subject identification information input device for inputting the test subject identification information, wherein when the test subject identification information of the test subject to be photographed is input by the test subject identification information input device, the positioning cautions presenting device reads the positioning cautions stored by being linked with the input test subject identification information from the positioning cautions storing device, and presents the read positioning cautions.

Specifically, in the positioning cautions storing device, the positioning cautions created with respect to the medical image photographed in the past, and the test subject identification information for identifying the test subject corresponding to the medical image are stored by being linked with each other. When the test subject identification information of the test subject to be photographed is input, the photographer can receive presentation of the positioning cautions stored by being linked with the input test subject identification information.

The apparatus for aiding photographing of the medical image according to the fourth aspect of the present invention, in the apparatus according to the first or second aspect, further includes an evaluation result storing device for storing test subject identification information for identifying the test subject corresponding to the medical image and the evaluation result evaluated for the medical image by the positioning evaluating device by linking the test subject identification information and the evaluation result with each other; and a test subject identification information input device which inputs the test subject identification information, wherein when the test subject identification information of the test subject to be photographed is input by the test subject identification information input device, the positioning cautions creating device reads the evaluation result stored by being linked with the input test subject identification information from the evaluation result storing device, and creates the positioning cautions based on the read evaluation result.

The fourth aspect of the present invention differs from the third aspect of the invention in the point that the test subject identification information and the evaluation result are linked with each other and stored in the evaluation result storing device. When the photographer inputs the test subject identification information of the test subject to be photographed, the evaluation result stored by being linked with the input test subject identification information is read from the evaluation result storing device, and the photographer can receive the presentation of the positioning cautions created based on the evaluation result.

The apparatus for aiding photographing of the medical image according to the fifth aspect of the present invention, in the apparatus according to the first or the second aspect, further includes an image storing device for storing the medical image and test subject identification information for identifying the test subject corresponding to the medical image by linking the medical image and the test subject identification information with each other; and a test subject identification information input device for inputting the test subject identification information, wherein when the test subject identification information of the test subject to be photographed is input by the test subject identification information input device, the image acquiring device acquires the medical image stored by being linked with the input test subject identification information from the image storing device.

The fifth aspect of the present invention differs from the third and the fourth aspects of the invention in the point in which the test subject identification information and the medical image are linked with each other and stored in the image storing device. When the photographer inputs the test subject identification information of the test subject to be photographed, the medical image stored by being linked with the input test subject identification information is read from the image storing device, and the photographer can receive the presentation of the positioning cautions for the medical image.

According to the third, fourth or fifth aspect of the present invention, there is provided the effect of being able to confirm the positioning cautions due to the physique or the like of the test subject before photographing by inputting the test subject identification information.

The apparatus for aiding photographing of the medical image according to the sixth aspect of the present invention, in the apparatus according to any one of the first to fifth aspects, further includes a positioning cautions storing device for storing photographer identification information for identifying a photographer who photographed the medical image, and positioning cautions created for the medical image by the positioning cautions creating device by linking the photographer identification information and the positioning cautions with each other; and a photographer identification information input device which inputs the photographer identification information, wherein when the photographer identification information is input by the photographer identification information input device, the positioning cautions presenting device reads the positioning cautions stored by being linked with the input photographer identification information from the positioning cautions storing device, and presents the read positioning cautions.

The apparatus for aiding photographing of the medical image according to the seventh aspect of the present invention, in the apparatus according to third aspect, further includes a photographer identification information input device which inputs a photographer identification information for identifying a photographer who photographed the medical image, wherein the positioning cautions storing device stores the photographer identification information, and the positioning cautions created for the medical image by the positioning cautions creating device by linking the photographer identification information and the positioning cautions with each other, and wherein when the photographer identification information is input by the photographer identification information input device, the positioning cautions presenting device reads the positioning cautions stored by being linked with the input photographer identification information from the positioning cautions storing device, and presents the read positioning cautions.

The apparatus for aiding photographing of the medical image according to the eighth aspect of the present invention, in the apparatus according to any one of the first to fifth aspects, further includes an evaluation result storing device for storing photographer identification information for identifying a photographer who photographed the medical image, and evaluation result evaluated for the medical image by the positioning evaluating device by linking the photographer identification information and the evaluation result with each other; and a photographer identification information input device for inputting the photographer identification information, wherein when the photographer identification information is input by the photographer identification information input device, the positioning cautions creating device reads the evaluation result stored by being linked with the input photographer identification information from the evaluation result storing device, and creates the positioning cautions based on the read evaluation result.

The apparatus for aiding photographing of the medical image according to the ninth aspect of the present invention, in the apparatus according to the fourth aspect, further includes a photographer identification information input device for inputting a photographer identification information for identifying a photographer who photographed the medical image, wherein the evaluation result storing device stores the photographer identification information, and the evaluation result evaluated for the medical image by the positioning evaluating device by linking the photographer identification information and the evaluation result with each other, and wherein when the photographer identification information is input by the photographer identification information input device, the positioning cautions creating device reads the evaluation result stored by being linked with the input photographer identification information from the evaluation result storing device, and creates the positioning cautions based on the read evaluation result.

The apparatus for aiding photographing of the medical image the tenth aspect of the present invention, in the apparatus according to any one of the first to fifth aspects, further includes an image storing device for storing the medical image and photographer identification information for identifying a photographer who photographed the medical image by linking the medical image and the photographer identification information with each other; and a photographer identification information input device for inputting the photographer identification information, wherein when the photographer identification information is input by the photographer identification information input device, the image acquiring device acquires the medical image corresponding to the input photographer identification information from the image storing device.

The apparatus for aiding photographing of the medical image the eleventh aspect of the present invention, in the apparatus according to the fifth aspects, further includes a photographer identification information input device for inputting a photographer identification information for identifying a photographer who photographed the medical image, wherein the image storing device for stores the medical image and the photographer identification information by linking the medical image and the photographer identification information with each other, and wherein when the photographer identification information is input by the photographer identification information input device, the image acquiring device acquires the medical image corresponding to the input photographer identification information from the image storing device.

In the third, fourth or fifth aspect of the invention, the positioning cautions, the evaluation results or the medical images are stored by being linked with the test subject identification information, whereas the sixth, seventh, eighth, ninth, tenth or eleventh aspect of the invention differs in the point in which the positioning cautions, evaluation results, or medical images are stored by being linked with the photographer identification information.

According to the sixth, seventh, eighth, ninth, tenth or eleventh aspect of the present invention, the photographer can confirm the positioning cautions due to his or her own drawback, habit or the like of positioning at the time of photographing before photographing, by inputting the photographer identification information. The positioning technique greatly varies depending on the photographers, and therefore, the apparatus is effective when a plurality of photographers perform photographing respectively.

The apparatus for aiding photographing of the medical image according to the twelfth aspect of the present invention is, in the apparatus according to any one of the first to eleventh aspects, the apparatus wherein the positioning evaluating device comprises a structure extracting device for extracting an anatomical structure from the acquired medical image, and evaluates whether the medical image is photographed by being properly positioned on the basis of the extracted structure.

The apparatus for aiding photographing of the medical image according to the thirteenth aspect of the present invention is, in the apparatus according to the twelfth aspect, the apparatus wherein the medical image is a breast image photographed by a mammography apparatus, and the structure extracting device extracts at least a breast, a mammary gland, a greater pectoral muscle and a nipple as the extracted structure.

The apparatus for aiding photographing of the medical image the fourteenth aspect of the present invention is, in the apparatus according to the thirteenth aspect, the apparatus wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image.

The apparatus for aiding photographing of the medical image according to the fifteenth aspect of the present invention is, in the apparatus according to the fourteenth aspect, the apparatus wherein the positioning evaluating device evaluates the symmetry respectively based on an area ratio of left and right breasts, an area ratio of left and right mammary glands, and an area ratio of left and right greater pectoral muscles which are extracted from the breast image, and the positioning evaluating device makes an evaluation with respect to the first positioning evaluation item based on evaluation result of the symmetry.

The apparatus for aiding photographing of the medical image the sixteenth aspect of the present invention is, in the apparatus according to the fourteenth or fifteenth aspect, the apparatus wherein the positioning evaluating device makes evaluation with respect to the second positioning evaluation item based on whether or not the left and right nipples can be extracted from the breast images. Unless the nipples are not extracted on the side surfaces, the nipples are likely to overlap the mammary glands and to be erroneously seen as abnormality in the mammary glands, or lesions directly under the nipples are likely to be missed.

The apparatus for aiding photographing of the medical image according to the seventeenth aspect of the present invention is, in the apparatus according to any one of the fourteenth to sixteenth aspects, the apparatus wherein the positioning evaluating device makes evaluation with respect to the third positioning evaluation item based on a lower end position of the greater pectoral muscle extracted from the breast image, a shape of the greater pectoral muscle, and an area ratio of the greater pectoral muscle to the breast. Evaluation is made based on, for example, the references that the lower end position of the greater pectoral muscle is photographed to the height of the nipple, and that the greater pectoral muscle draws a slightly projected arc, and that the greater pectoral muscle is not too large with respect to the size of the breast (if the greater pectoral muscle is included too much, compression on the mammary gland becomes weak, and the entire mammary gland is not within the irradiation field).

The apparatus for aiding photographing of the medical image according to the eighteenth aspect of the present invention is, in the apparatus according to any one of the fourteenth to seventeenth aspects, the apparatus wherein the positioning evaluating device makes evaluation with respect to the fourth positioning evaluation item based on a length of a line composed of a boundary of the greater pectoral muscle extracted from the breast image and an image end at a side of a chest wall, and a length of the mammary gland extracted from the breast image which overlaps the line. Thereby, it is evaluated whether the fat tissue behind the mammary gland is continuously visualized (whether the entire mammary gland is visualized).

The apparatus for aiding photographing of the medical image according to the nineteenth aspect of the present invention is, in the apparatus according to any one of the fourteenth to eighteenth aspects, the apparatus wherein the positioning evaluating device comprises a detecting device for detecting a skin line of the breast image, and makes evaluation with respect to the fifth positioning evaluation item based on the shape of the detected skin line. Thereby, it is evaluated whether the abdominal tissue is included (whether the lower end of the mammary gland is within the photographing range).

The apparatus for aiding photographing of the medical image according to the twentieth aspect of the present invention is, in the apparatus according to any one of the fourteenth to nineteenth aspects, the apparatus wherein the positioning evaluating device comprises a calculating device for calculating a contrast value in the mammary gland of the mammary gland extracted from the breast image, and makes evaluation with respect to the sixth positioning evaluation item based on an area ratio of the breast and the mammary gland except for the greater pectoral muscle extracted from the breast image, and the calculated contrast value in the mammary gland. Thereby, it is evaluated whether the mammary gland is sufficiently compressed and extended. There is the correlation between the area ratio (mammary gland ratio) of the breast and the mammary gland except for the greater pectoral muscle and the contrast value in the mammary gland, and when the contrast in the mammary gland is low with respect to the mammary gland ratio, extension and compression of the mammary gland are considered to be insufficient.

A computer program product for aiding photographing of a medical image according to the twenty-first aspect of the present invention, includes: a computer readable storage medium having computer readable program code embodied therein, the computer readable program code comprising: computer-readable program code for causing a computer to acquire a medical image obtained by radiation-photographing a part including a diagnosis target part of a test subject; computer-readable program code for causing a computer to analyze the acquired medical image and to evaluate positioning of the test subject at a time of the radiation-photographing; computer-readable program code for causing a computer to create positioning cautions based on the evaluation result; and computer-readable program code for causing a computer to present the created positioning cautions.

According to the present invention, the positioning cautions which are automatically created from the evaluation result obtained by analysis of the medical image are presented for the medical image (including the medical image after photographing) of the past. Therefore, the points to be improved of positioning at the time of photographing of the next medical image can be easily grasped, suitable positioning for each of the test subject can be aided, and the photographing technique of the photographer can be improved.

BRIEF DESCRIPTION OF THE DRAWINGS

FIGS. 5A to 5C are diagrams showing an evaluation procedure of positioning by a positioning evaluating device according to the present invention;

FIG. 10 is a table summarizing each evaluation item of positioning and its evaluation point;

DETAILED DESCRIPTION OF THE PREFERRED EMBODIMENTS

Hereinafter, preferred embodiments of an apparatus for aiding photographing of a medical image and a computer program product for the same according to the present invention will be described in accordance with the attached drawings.

[Apparatus Configuration]

Figure 1:
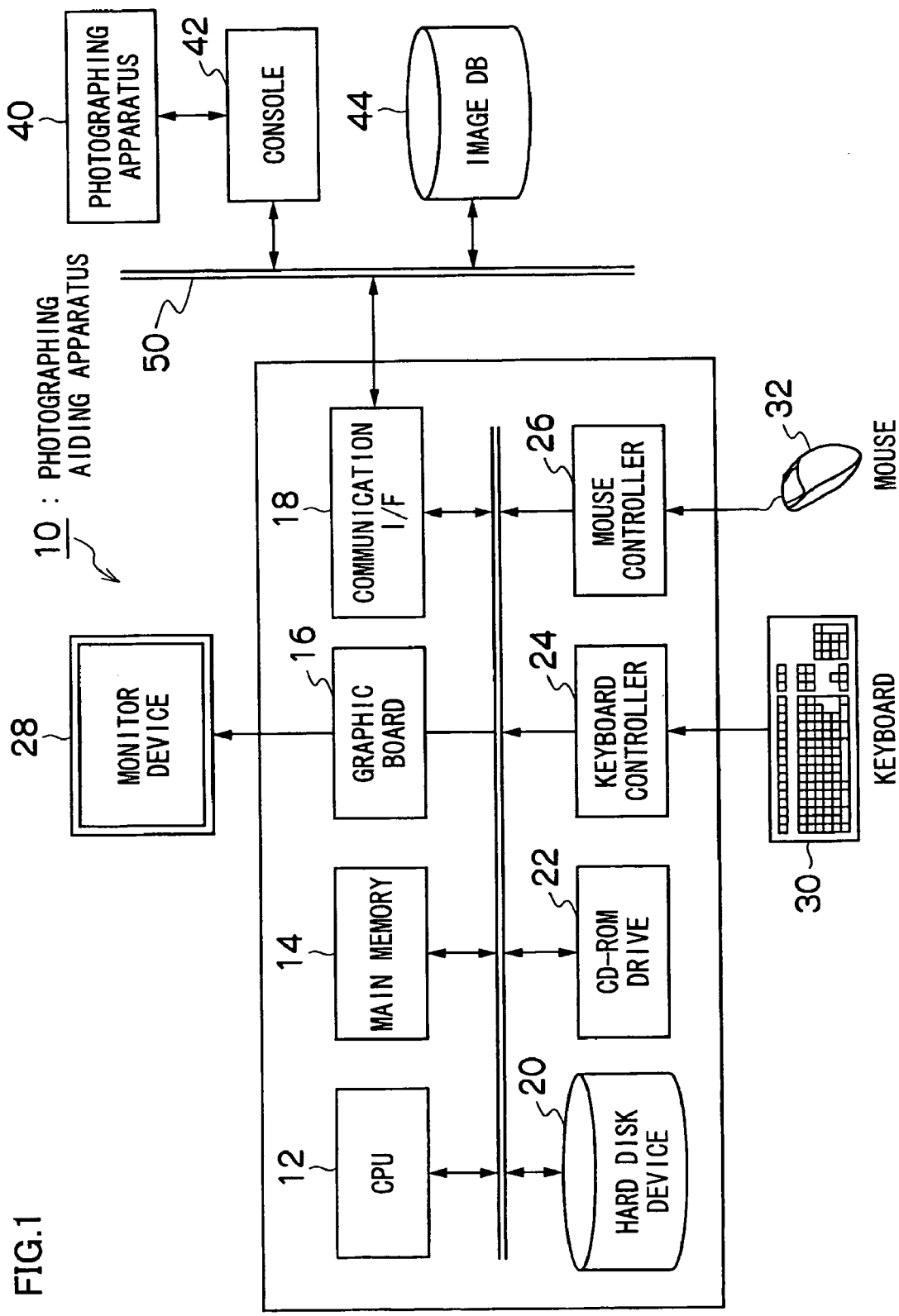
FIG. 1 is a system configuration diagram including an apparatus for aiding photographing of a medical image according to the present invention.

FIG. 1 is a system configuration diagram including an apparatus for aiding photographing of a medical image according to the present invention.

The system includes a photographing aiding apparatus 10 for a medical image according to the present invention, a photographing apparatus 40 photographing a medical image, which is installed in a medical facility or the like, a console 42 for performing operation or the like of the photographing apparatus 40, and an image database (image DB) 44 storing a medical image photographed by the photographing apparatus 40.

The photographing aiding apparatus 10 is a computer such as a workstation, and includes a central processing unit (CPU) 12 which controls the operation of each component, a main memory 14 which stores a control program of the apparatus and becomes an operation region at a time of execution of the program, a graphic board 16 which controls display of a monitor device 28 such as a liquid crystal display and a CRT display, a communication interface (communication I/F) 18 connected to a network 50 of the medical facility, a hard disk device 20 storing various kinds of application software including a photographing aiding program for a medical image according to the present invention and an image analyzing program, positioning cautions which will be described later, a positioning evaluation result and the like, a CD-ROM drive 22, a keyboard controller 24 which detects a key operation of a keyboard 30 and outputs the key operation to the CPU 12 as an instruction input, and a mouse controller 26 which detects a state of a mouse 32 as a position input device and outputs signals of a position of the mouse pointer on the monitor device 28, a state of the mouse 32 and the like to the CPU 12.

The photographing apparatus 40 is a mammography apparatus which performs radiation-photographing of a breast image in this embodiment.

<Mammography Apparatus>

Figure 2:
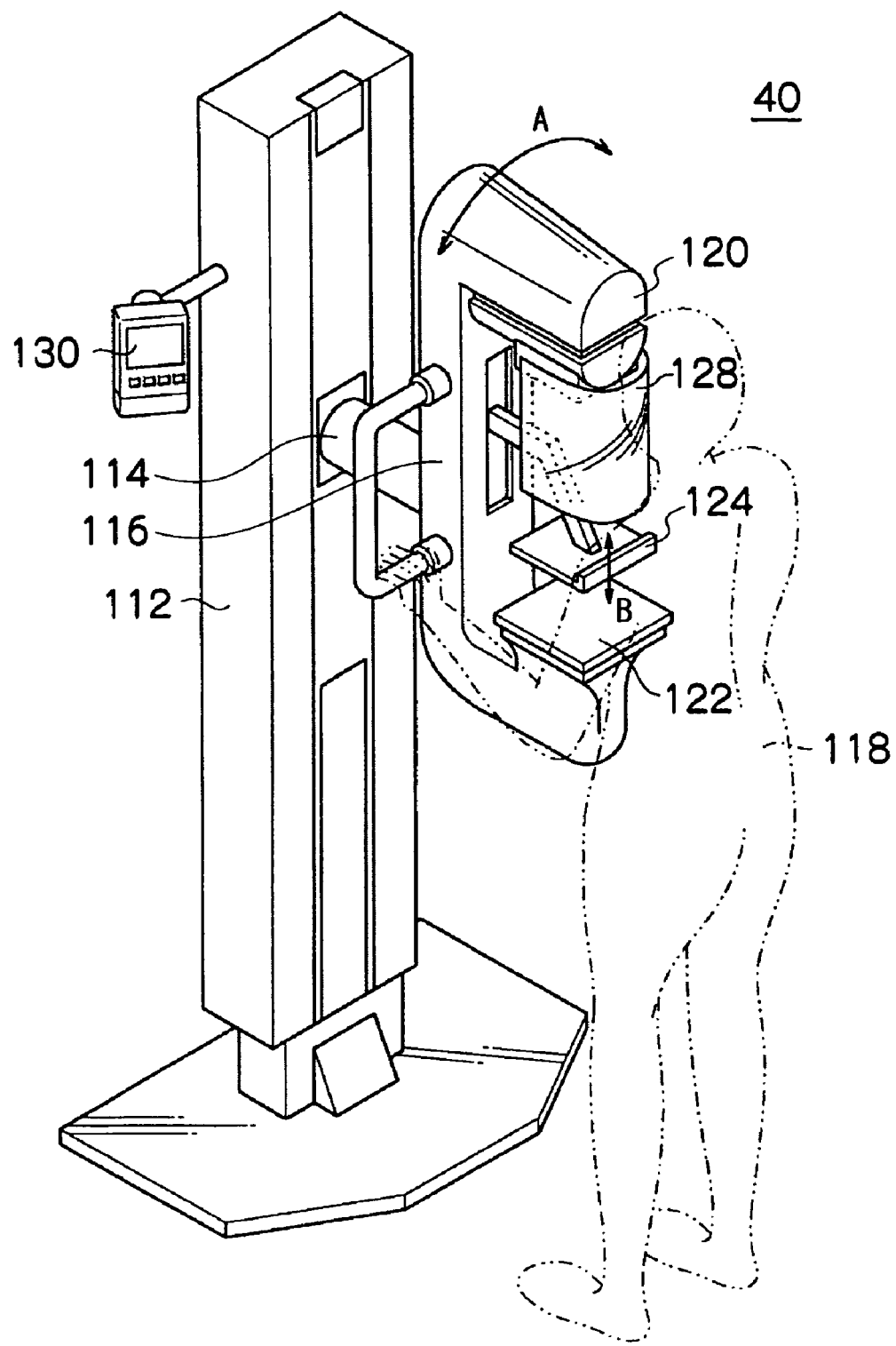
FIG. 2 is a configuration diagram showing an embodiment of a photographing apparatus (mammography apparatus)

FIG. 2 is a configuration diagram showing an embodiment of the photographing apparatus (mammography apparatus) 40.

The mammography apparatus 40 includes a base 112 which is installed in a vertical state, an arm member 116 which is fixed to a turn shaft 114 placed at a substantially central portion of the base 112, a radiation source housing section 120 which houses a radiation source for irradiating the breast of a test subject 118 with radioactive rays, and is fixed to one end portion of the arm member 116, a photographing table 122 which houses a solid state detector for detecting the radioactive rays transmitting through the breast and acquiring a radiological image information, and is fixed to the other end portion of the arm member 116, and a compression plate 124 which compresses the breast against the photographing table 122.

The arm member 116 to which the radiation source housing section 120, the photographing table 122 and the compression plate 124 is configured so that the photographing direction with respect to the breast of the test subject 118 is adjustable, by turning the arm member 116 according to the arrow A direction around the turn shaft 114. The compression plate 124 is placed between the radiation source housing section 120 and the photographing table 122 in the state in which the compression plate 124 is connected to the arm member 116, and is configured to be able to move along the arrow B direction.

A face guard sheet 128 which includes a member for shielding the radioactive rays is placed at the radiation source housing section 120 in order to protect the region in the vicinity of the face of the test subject 118 from irradiation of the radioactive rays. Further, in the base 112, a display device 130 is placed, and the display device 130 displays the photographing information such as the photographed part of the test subject 118, and the photographing direction, ID information of the test subject 118 and the like, and displays information relating to the compression remaining time until the compression state of the breast by the compression plate 124 is released in accordance with necessity.

Figure 3:
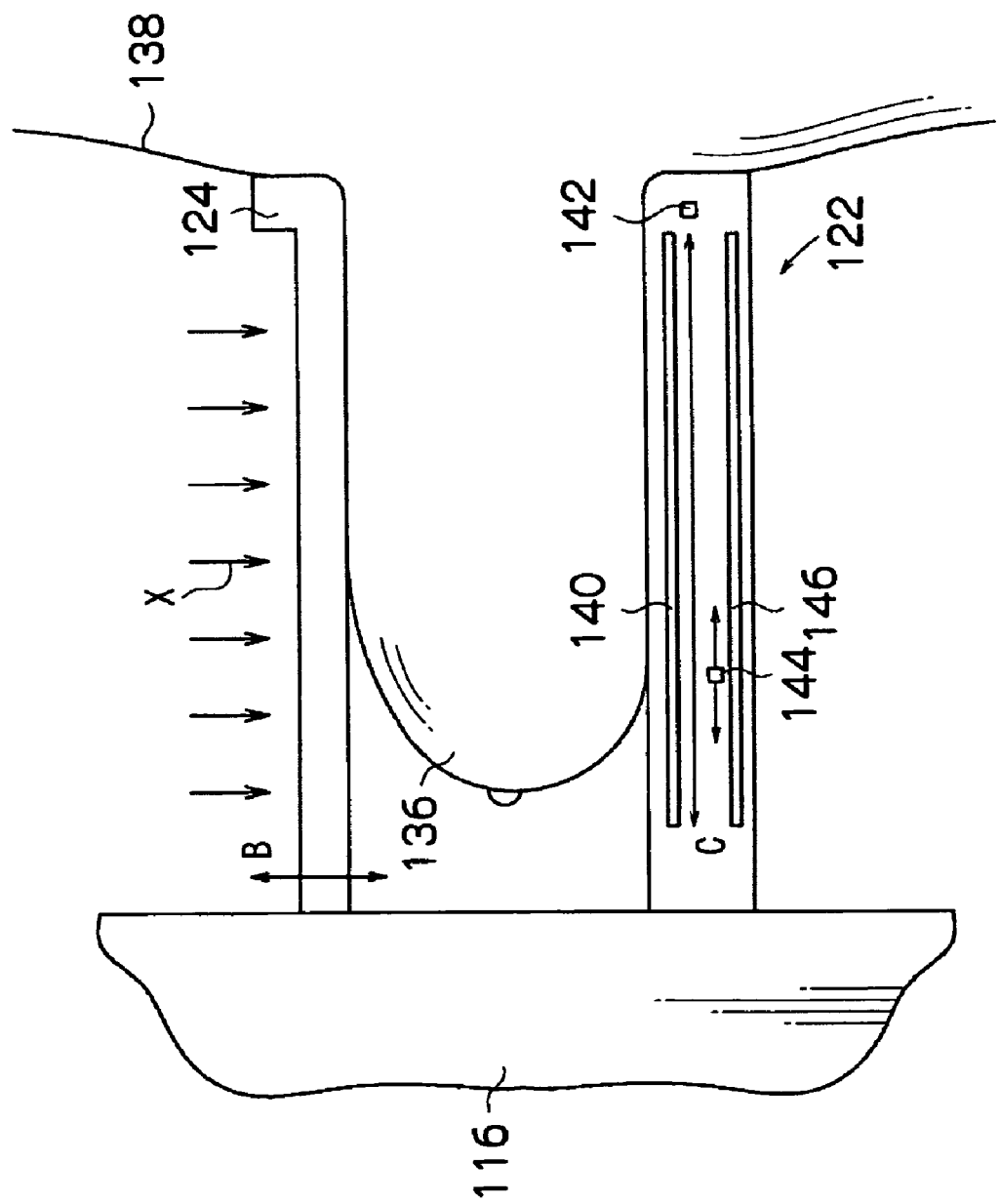
FIG. 3 is an internal configuration diagram of a photographing table in the mammography apparatus.

FIG. 3 is an internal configuration diagram of the photographing table 122 in the mammography apparatus 40, and shows the state in which a breast 136 which is a photographed part of the test subject 118 is disposed between the photographing table 122 and the compression plate 124. Reference numeral 138 designates a chest wall of the test subject 118.

The photographing table 122 includes therein a solid state detector 140 (radiological image information detector) which accumulates the radiological image information based on radioactive rays X transmitted through the breast 136, and outputs the information as an electric signal, a read light source section 142 which irradiates the solid state detector 140 with read light to read the radiological image information accumulated and recorded in the solid state detector 140, a dose detector (a radioactive rays detector for automatic exposure controlling, hereinafter, called "AEC (Automatic Exposure Control) sensor 144") which detects the dose of the radioactive rays X transmitted through the breast 136 to determine irradiation time which is one of the irradiation conditions of the radioactive rays X, and an erasing light source section 146 which irradiates the solid state detector 140 with erasing light to remove unnecessary electric charges accumulated in the solid state detector 140.

The solid state detector 140 is a direct conversion type radiological solid state detector and is a light reading type radiological solid state detector. The solid state detector 140 accumulates the radiological image information based on the radioactive rays X transmitted through the breast 136 as an electrostatic latent image, and generates an electric current corresponding to the electrostatic latent image by being scanned with read light from the read light source section 142.

The read light source section 142 includes a line light source including a plurality of LED chips arranged in line, and an optical system which linearly irradiates the solid state detector 140 with the read light output from the line light source. The read light source section 142 exposes and scans the entire surface of the solid state detector 140 by moving the line light source in which the LED chips are arranged in the direction orthogonal to the extending direction of a linear electrode which is a second conductor layer of the solid state detector 140, along the extending direction (arrow C direction) of the linear electrode.

The AEC sensor 144 is movable in the arrow C direction along the solid state detector 140 so as to be able to detect the dose of the radioactive rays X by being moved to the part corresponding to the portion with high mammary gland density of the breast 136, for example. The erasing light source section 146 includes very small LED chips which are arranged, emit/erase light in a short time, and have very small afterglow in the two-dimensional state.

The radioactive rays X transmitted through the breast 136 are detected as the radiological image information by the solid state detector 140, and the radiological image of the breast 136 is formed by a radiological image forming section (not illustrated). Meanwhile, the solid state detector 140 from which the radiological image information is read is irradiated with the erasing light from the erasing light source section 146, and thereby, erasing processing of the remaining radiological image information is performed.

When mammography of the test subject 118 is performed, the test subject 118 is positioned, and is photographed by operating the console 42 (FIG. 1). Further, the console 42 includes an input device which inputs test subject identification information (test subject ID) for identifying the test subject, and a photographer ID for identifying the photographer, and the test subject ID and the photographer ID which are input by the input device and a medical image photographed by the photographing apparatus 40 are linked with one another, and are stored in the image DB 44. The date and year of photographing are linked to the photographed medical image and are also stored.

Next, the procedure of positioning and photographing the test subject 118 will be described.

The photographer (radiological technician) sets the mammography apparatus 40 in a predetermined state in accordance with the specified photographing method. For example, as the photographing direction of the breast 136, craniocaudal (CC) photographing for performing photographing by irradiating the breast 136 with radioactive rays X from above, mediolateral (ML) photographing for performing photographing by irradiating the breast 136 with radioactive rays X from a side surface of the breast 136, and mediolateral oblique (MLO) photographing for performing photographing by irradiating the breast 136 with the radioactive rays X from an oblique direction are cited. The arm member 116 is turned around the turn shaft 114 in accordance with these photographing directions. FIG. 2 shows the case of performing craniocaudal (CC) photographing.

After the above preparation operation is completed, the test subject 118 is guided to the mammography apparatus 40, and the positioning of the breast 136 is started. Specifically, the radiological technician turns on a compression plate moving switch (not illustrated) after placing the breast 136 put on the photographing table 122, to move the compression plate 124 along the arrow B direction (FIG. 2) toward the photographing table 122 in order to compress the breast 136 gradually.

When a pressure sensor (not illustrated) detects that the compression pressure reaches a compression pressure required for photographing, movement of the compression plate 124 is stopped, and photographing permission is output.

When the photographer (the radiological technician) turns on an irradiation switch (not illustrated), radiation photographing of the breast 136 is performed.

When mammography is completed, compression on the breast 136 is released by moving the compression plate 124 in the direction to be away from the photographing table 122. In photographing of the breast 136, plurality of kinds of photographing, such as CC photographing, ML photographing and MLO photographing of left and right breasts 136 are performed with respect to one test subject 118.

Returning to FIG. 1, the photographing aiding apparatus 10 includes a positioning evaluating device which analyzes the photographed medical image, evaluates (quantifies) the positioning according to each of items of a plurality of kinds of positioning at a time of radiation photographing, and outputs an evaluation result according to each of the items. The positioning evaluating device includes a structure extracting program for analyzing the medical image and extracting an anatomical structure from the medical image, and an evaluating program for evaluating whether the test subject 118 is suitably positioned at the time of photographing the medical image on the basis of the extracted structure. The positioning evaluating device is realized by execution of these programs.

Further, the photographing aiding apparatus 10 includes a positioning cautions creating device which creates positioning cautions such as points to be improved of positioning based on the evaluation result of positioning evaluated by the positioning evaluating device. The positioning cautions creating device has a database in which evaluation points (evaluation points including combination of a plurality of items) according to each item of positioning and the positioning cautions are stored by being linked to each other in advance. When receiving the evaluation result of positioning relating to a certain medical image from the positioning evaluating device, the positioning cautions creating device extracts the positioning cautions corresponding to the evaluation result from the database.

The positioning cautions created by the above described positioning cautions creating device are displayed on the monitor device 28 and are presented to the photographer.

Further, the positioning cautions created as described above are linked with the test subject ID and the photographer ID and are stored in the positioning cautions storing device (hard disk device 20).

The keyboard 30 and the mouse 32 function as the information input device for inputting the test subject ID and the photographer ID. When the test subject ID and the photographer ID are input by the information input device, the positioning cautions with respect to the medical image of the past which are stored by being linked with the information are read out from the positioning cautions storing device, and the read positioning cautions are displayed on the monitor device 28.

[Evaluating Method of Positioning]

Next, an evaluating method of positioning by the positioning evaluating device will be described.

According to the facility image evaluation of The Central Committee on Quality Control of Mammographic Screening, A Nonprofit Organization in Japan, positioning is evaluated with six items each items evaluated on a 4-point scale, and a total point is 24. The evaluation items are shown in FIG. 4 and [Table 1].

TABLE 1

| EVALUATION ITEM | DESCRIPTION |
| --- | --- |
| (1) Lateral symmetry | Photograph of left and right breasts shall be symmetrical. Important in comparative reading. |
| (2) Lateral orientation of nipple | Nipple shall be visualized directly from right angles. Unless nipple is not oriented to side, nipple overlaps mammary gland and is likely to be erroneously considered as abnormality in mammary gland, and lesion directly under nipple is likely to be missed. |
| (3) Greater pectoral muscle | In MLO, breast shall be photographed substantially to height of nipple, greater pectoral muscle shall draw substantially projected arc, and shall not be too large relative to size of breast. If greater pectoral muscle is excessively included, compression on mammary gland becomes weak, and entire mammary glands are not included in irradiation field. |
| (4) Space behind mammary gland | Fat tissue behind mammary gland shall be visualized without being discontinued. This becomes indicator of whether entire mammary gland is visualized or not. |
| (5) Part under breast | Abdominal tissue shall be included. This becomes indicator of whether lower end of mammary gland is included in photographing range. |
| (6) Extension of mammary gland | Mammary glands shall be sufficiently compressed and extended. |

Figure 4:
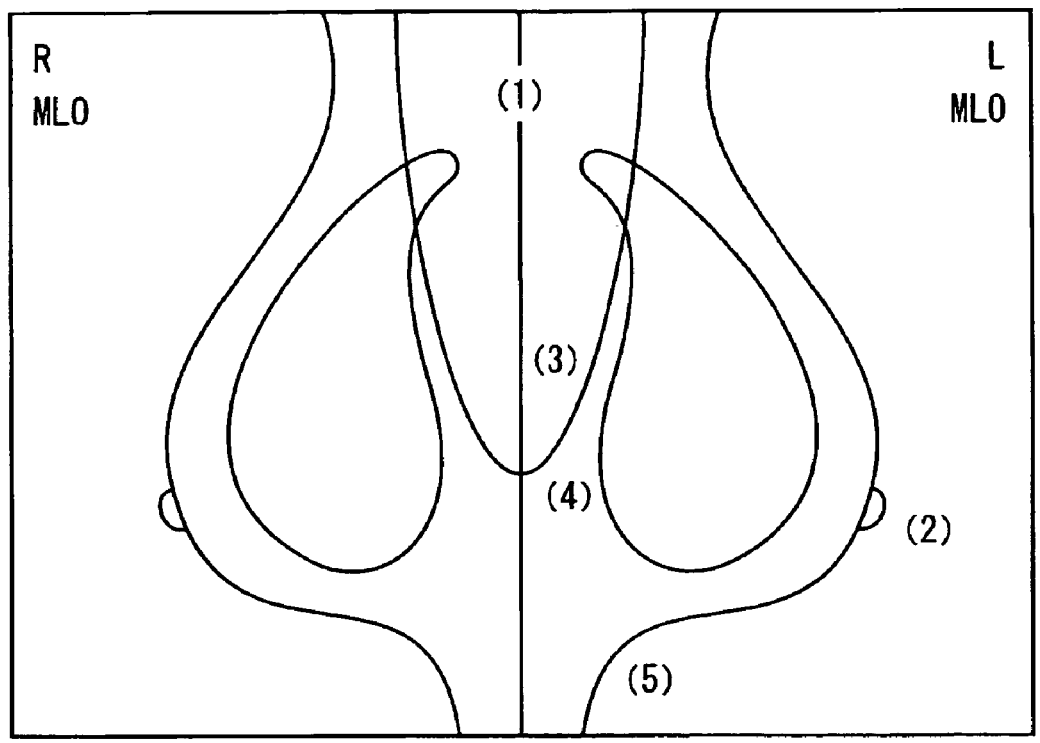
FIG. 4 is a diagram showing each part relating to positioning evaluation item of a breast image.

FIG. 4 is cited from the following Non-Patent Document 1, and shows the part of each of the items of the above described [Table 1], "Non-Patent Document 1: "Shinryou Houshasen Gishi ni Shitte Hoshii Gazou Shindan Nyubou", Author: Tokiko ENDO, Publisher: Iryou Kagaku Co., p. 18, FIG. 16".

FIGS. 5A, 5B and 5C are diagrams showing an evaluation procedure of positioning by the aforementioned positioning evaluating device.

As shown in FIGS. 5A, 5B and 5C, the positioning evaluating device takes in a breast image (medical image) which is an evaluation target (FIG. 5A), analyzes the medical image, and extracts an anatomical structure (breast, mammary glands, a greater pectoral muscle, a nipple and the like) from the medical image (FIG. 5B).

In this case, "an anatomical structure" means a structure such as organs configuring a human body such as the greater pectoral muscle and the breast. Each of the structures appears on the image with its peculiar density value, shape and position, and therefore, can be extracted correspondingly with the information such as the density value, shape and position.

Figure 6B:
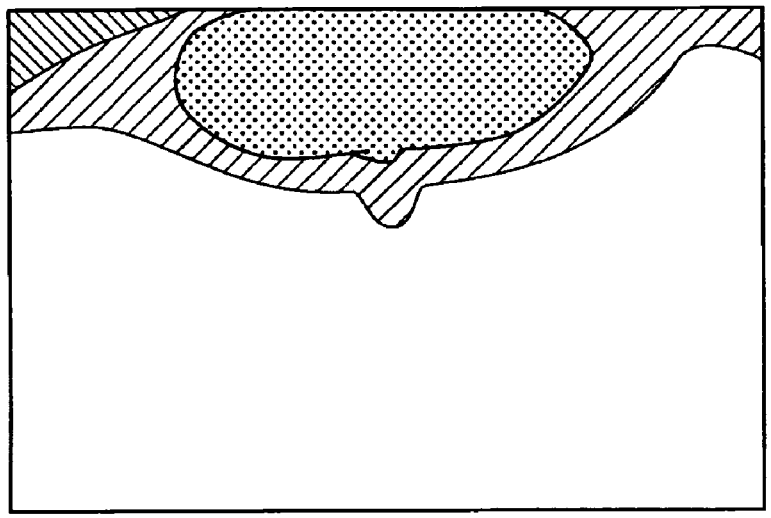
FIG. 6B is a diagram showing an image with a region divided for each structure extracted from the original image.
Figure 6A:
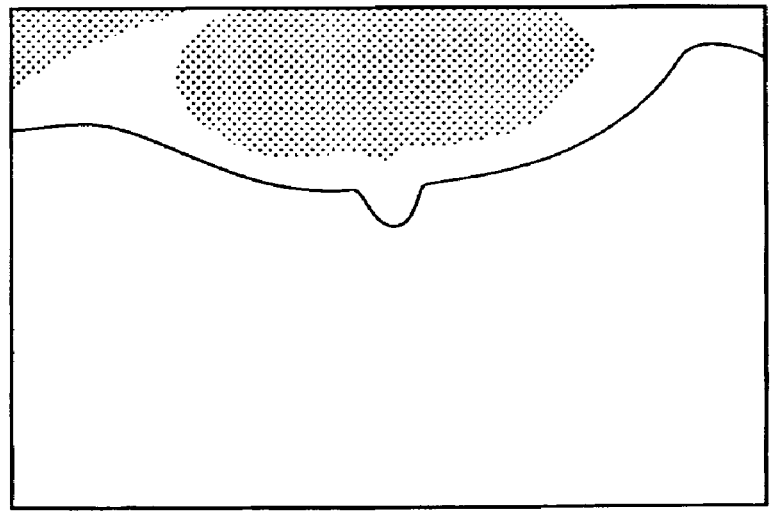
FIG. 6A is a diagram showing an original image of a breast image.

FIG. 6A shows an original image of the breast image, and FIG. 6B shows an image of the region which is divided according to the structures extracted from the original image.

More specifically, each of the structures is extracted in the following sequence (for details, refer to Japanese Patent Application Laid-Open No. 2005-65855 and Japanese Patent Application Laid-Open No. 2006-68373 which are filed to the Japan Patent Office by the applicant).

(i) The image is divided into a breast region and a void region. The void region shows especially high density on the image, and therefore, a peak which appears at the high density side in the density histogram of the entire image corresponds to the void region. By performing binarization processing with use of the value obtained by subtracting a fixed value from the peak value as a threshold value, the image is divided into the breast region and the void region.

(ii) The outline of the breast region (hereinafter, called a skin line) is extracted. The boundary points (pixels) between the breast region and the void region are sequentially searched, and the searched pixels are connected to extract the skin line.

(iii) A greater pectoral muscle region is extracted. The boundary of the greater pectoral muscle and fat region has a relatively clear edge, and therefore, scanning by a differentiation operator is performed toward the chest wall side from the skin line, and the point having a large differential value is extracted as the boundary point of the greater pectoral muscle region. The curved line connecting the extracted boundary points is calculated, and the chest wall side (side opposite from the void region) with respect to the curved line is extracted as the greater pectoral muscle region.

(iv) The threshold value for extracting the mammary gland is calculated from the density values of the greater pectoral muscle region and the fat region in the vicinity of the greater pectoral muscle region, and the mammary gland region is extracted.

(v) A nipple portion is detected. A smoothed skin line is obtained by smoothing the skin line, and the nipple portion is detected based on the separation amount of the smoothed skin line and the skin line. When the nipple portion cannot be detected, the highest point is set as the nipple portion.

By extracting a plurality of structures, the characteristics of each of the structures (position, shape, size and the like) can be grasped from the relationship with the other structures, and the positioning evaluation thereafter can be performed with high precision.

Next, evaluation of each positioning item is performed (FIG. 5C). Evaluation of each positioning item is performed as shown as follows.

(1) Evaluation of Lateral Symmetry

Symmetry of the entire breast (2 points), symmetry of the mammary gland (1 point), and symmetry of the greater pectoral muscle (1 point) are evaluated, and lateral symmetry is evaluated with the total points (scale of 4 points). If the positioning at the time of photographing the left breast image and the positioning at the time of the right breast of the image are similar, the area of the structures in the left and right breast image should be substantially the same, and the symmetry is evaluated based on the area ratio of the structures in the left and the right images as in the following formula.

$$\text{Symmetry} = 1 - \frac{2 \times |(\text{area } A) - (\text{area } B)|}{(\text{area } A) + (\text{area } B)} \quad \text{[Expression 1]}$$

In the above described [Expression 1], (area A) expresses the area of each structure in the right breast image, and (area B) expresses the area of each structure in the left breast image. The points of the symmetry of the entire breasts are the result of the above expression×2. Further, when the evaluation point calculated by the equation of [expression 1] becomes negative, the evaluation point is set as zero point.

(2) Evaluation of the Lateral Orientation of Nipple

When the nipple portion can be detected, two points are given, whereas when the nipple portion cannot be detected, the nipple is considered to be completely inside, and zero point is given. Evaluation is performed for each of the left and right breasts, and evaluation is performed with the total points (scale of four points).

(3) Evaluation of Greater Pectoral Muscle

The position of the lower end portion of the greater pectoral muscle (one point), shape (0.5 points) and area (0.5 points) are respectively evaluated, and evaluation of the greater pectoral muscle is performed with the total points (two points for each of the left and right, a scale of four points in total). First, the position of the lower end portion of the greater pectoral muscle is desired to be photographed substantially to the height of the nipple. Evaluation is performed based on the following equation based on the positions of the lower end portion of the greater pectoral muscle and the nipple portion.

Evaluation point (position of the lower end portion of the grater pectoral muscle) = [Expression 2]

$$1 - \frac{2 \times |(\text{length } A) - (\text{length } B)|}{(\text{length } A) + (\text{length } B)}$$

In this case, (length A) expresses the length to the lower end portion of the greater pectoral muscle from the upper end of the image, and (length B) expresses the length to the nipple portion from the upper end of the image. When the evaluation point calculated by the equation of [expression 2] becomes negative, the evaluation point is set as zero point.

Further, the shape of the greater pectoral muscle is desirably in the projected shape. The greater pectoral muscle in the recessed shape means that the pectoral muscle is not suitably moved inside at the time of positioning, or that the pectoral muscle is fastened by elevation or outward swing of the upper arms of the test subject. The shape of a greater pectoral muscle can be expressed by a quadratic function, and therefore, it can be determined whether the greater pectoral muscle is in the projected shape or the recessed shape with respect to the chest wall side based on the coefficients of the quadratic function. The shape evaluation point is calculated as 0.5 points in the case of the projected shape, and 0 point in the case of the recessed shape.

The area of the greater pectoral muscle is desirably in the range of 10% to 50% with respect to the area of the entire breast. Thus, the area evaluation point is calculated as 0.5 points in the case that the area of the greater pectoral muscle is within the range, and as zero point in the case that the area of the greater pectoral muscle is outside the range.

(4) Evaluation of the Space Behind the Mammary Gland

This is the evaluation item of whether the entire mammary gland is visualized, and according to this, it is analyzed whether fat is visualized behind the mammary gland. More specifically, the evaluation of the space behind the mammary gland is performed according to the following equation based on the degree of overlapping of the line (boundary of the greater pectoral muscle and the image end at the side of the chest wall) shown by the dotted line of FIG. 7 and the mammary gland.

Evaluation point (space behind the mammary gland) = [Expression 3]

$$2 \times \frac{(\text{length } B)}{(\text{length } A)}$$

Figure 7:
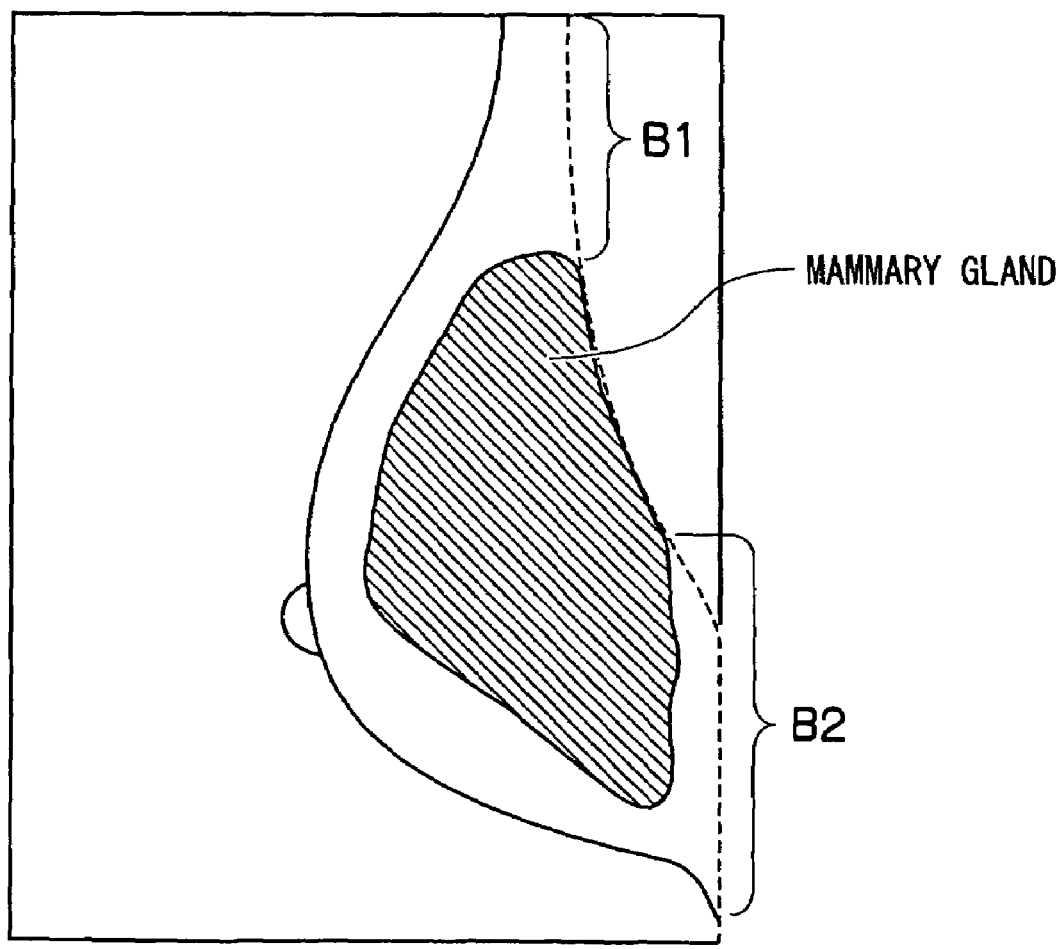
FIG. 7 is a diagram used for explaining evaluation of a space behind a mammary gland.

Here, the length of the dotted line of FIG. 7 is set as (length A), and the length except for the length of the portion overlapping the mammary gland on the dotted line is set as (length B (=B1+B2)). The evaluation points are calculated respectively based on the left and right breast images, and the evaluation of the space behind the mammary gland is performed with the total points (scale of 4 points).

(5) Evaluation of the Portion Under the Breast

It can be determined from the shape of the breast whether the abdominal tissue is included or not. More specifically, it is determined according to whether the skin line reaches the lower end of the image or not. When the skin line reaches the lower end, two points are given, and when it does not reach the lower end, zero point is given. The evaluation points are calculated respectively based on the left and right breast images, and the evaluation of the portion under the breast is performed with the total points (scale of 4 points).

(6) Evaluation of Extension of the Mammary Gland

Extension of the mammary gland is evaluated by calculating the area ratio (hereinafter, called "mammary gland ratio") of the mammary gland region with respect to the entire breast and a contrast value in the mammary gland. Here, the mammary gland ratio is calculated by the following equation.

Mammary gland ratio=(area of the mammary gland region)/(area of the entire breast except for the greater pectoral muscle) [Expression 4]

Further, the contrast value in the mammary gland can be calculated based on a local dispersion value in the mammary gland region as will be described hereinafter.

Figure 8:
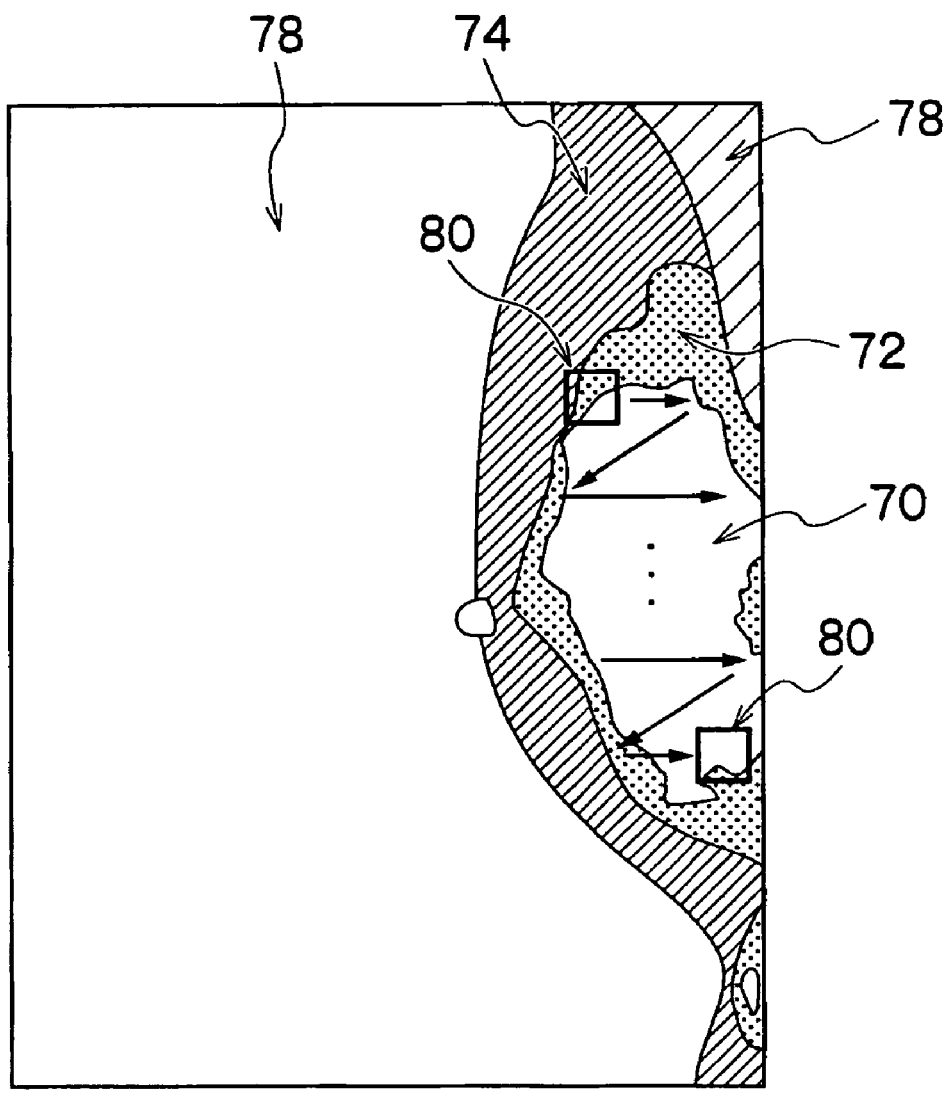
FIG. 8 is a diagram showing a state of setting local regions to a mammary gland region.

First, as shown in FIG. 8, a very small square region mainly covered by pixels belonging to the mammary gland region 70 is set as a local region 80. The size of the local region 80 is set to such a size as to include both the mammary gland structure and background. It is empirically preferable to set the size to the size of about 5 by 5 mm. As shown by the arrow in FIG. 8, it is scanned to an entire mammary gland region 70.

When the local region 80 is set, dispersion of the signal value is calculated in each local region 80 in order to calculate the contrast value of the mammary gland structure in the local region 80. The dispersion value does not have to be calculated for all the pixels of the mammary gland region 70, and about 500 points are empirically sufficient.

Further, when a void region 78, a fat region 74 in the vicinity of the skin and a greater pectoral muscle region 76 are included in the local region 80, the dispersion value sometimes becomes extremely large. Therefore, for calculation of the dispersion value, only the signal values of the mammary gland region 70 and the fat region 72 except for the region in the vicinity of the skin are used, and the signal values of the other regions are excluded.

By calculating the dispersion value in the local region 80 as described above, easiness to see the local mammary gland structure and lesion can be taken into consideration. Further, by calculating the dispersion value by including not only the signal value of only the inside of the mammary gland region 70 but also the signal value of the fat region 72 of the region except for the region in the vicinity of the skin, contrast of the mammary gland and the peripheral region (fat region 72) can be taken into consideration.

Dispersion of the signal value within the local region is calculated in order to calculate the contrast value within the local region, but the method is not limited to the one using dispersion, and the difference between the maximum value and the minimum value, the difference of the average signal values of the respective classes when dividing the values into two classes by a discrimination analysis method, and the like may be obtained.

The contrast value in the mammary gland is calculated. When the dispersion values are calculated in the respective local regions 80, the contrast value in the mammary gland of the image is calculated by integrating them. Here, the median value of a plurality of dispersion values is calculated, and it is set as the contrast value in the mammary gland.

Figure 9:
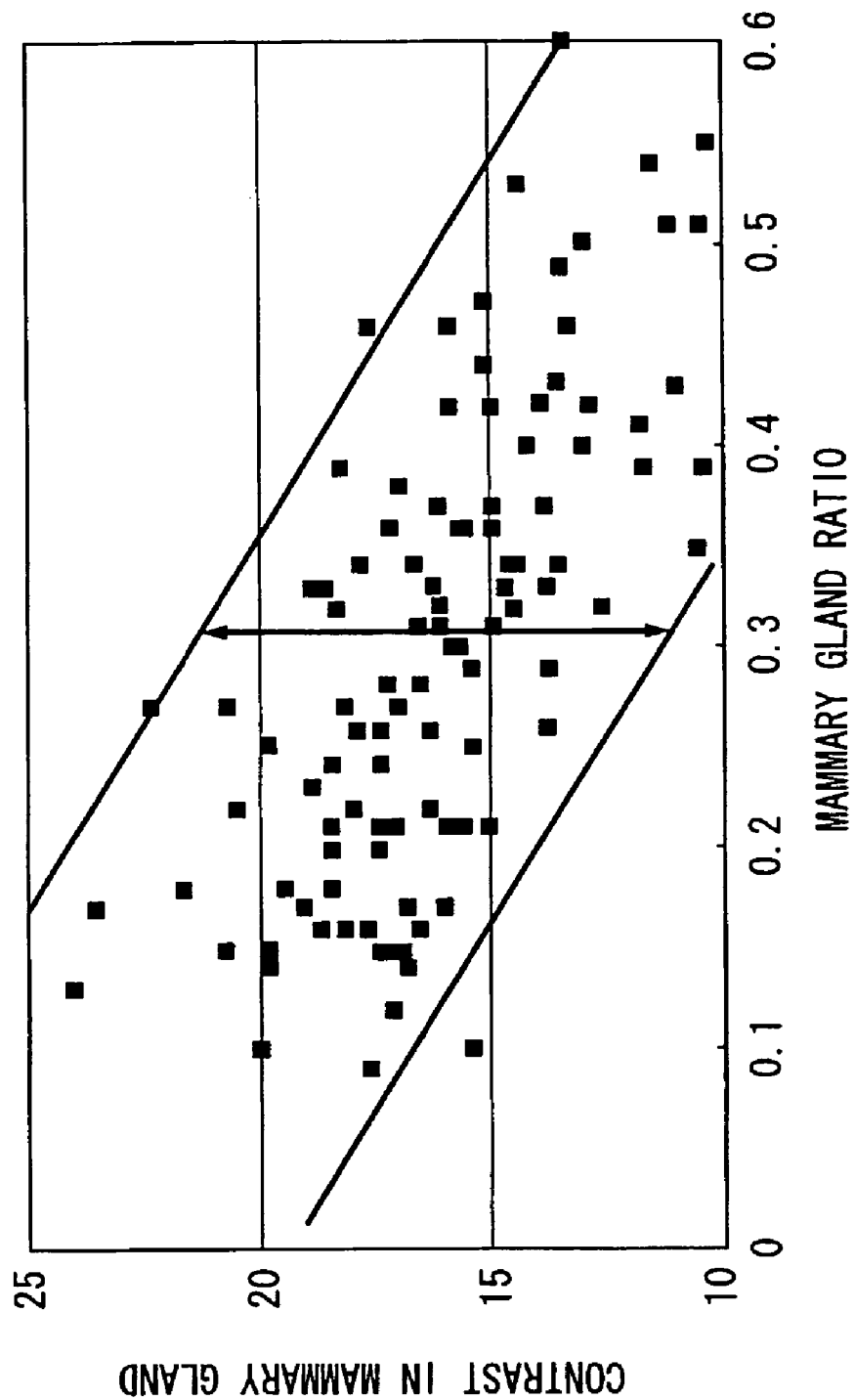
FIG. 9 is a diagram showing relationship of a mammary gland ratio and a contrast value in the mammary gland.

As a result of the study by the present inventor, it has been found out that correlation exists between the mammary gland ratio and the contrast value in the mammary gland as shown in FIG. 9. In the case of the contrast in the mammary gland which is a constant value or less with respect to the mammary gland ratio, extension and compression of the mammary gland are considered to be insufficient. Thus, the average value of the contrast value in the mammary gland and the standard deviation with respect to each of the mammary gland ratios are calculated from a number of images in advance, and from the standard deviation corresponding to the mammary gland ratio calculated from the equation of [expression 4], and the contrast value in the mammary gland, the extension of the mammary gland is evaluated in accordance with the following equations of [expression 5], [expression 6] and [expression 7].

Contrast value in the mammary gland<average value−
  (3×standard deviation)    [Expression 5]

Average value−(3×standard deviation)≦contrast value
  in mammary gland<average value−standard
  deviation    [Expression 6]

Average value−standard deviation≦contrast value in
  mammary gland    [Expression 7]

In the case of the above described equation of [expression 5], extension of the mammary gland is set as zero point, in the case of the equation of [expression 6], it is set as one point, and in the case of the equation of [expression 7], it is set as two points. The evaluation points are calculated respectively based on the left and right breast images, and extension of the mammary gland is evaluated with the total points (scale of four points).

The image contrast changes depending on the irradiation conditions of X-rays, and therefore, the above described average value and standard deviation may be obtained for each irradiation condition.

FIG. 10 is a table which summarizes the respective evaluation items of positioning and the evaluation points as described above, and shows the case of six items each with the scale of four points, the total scale of 24 points.

First Embodiment

Figure 11:
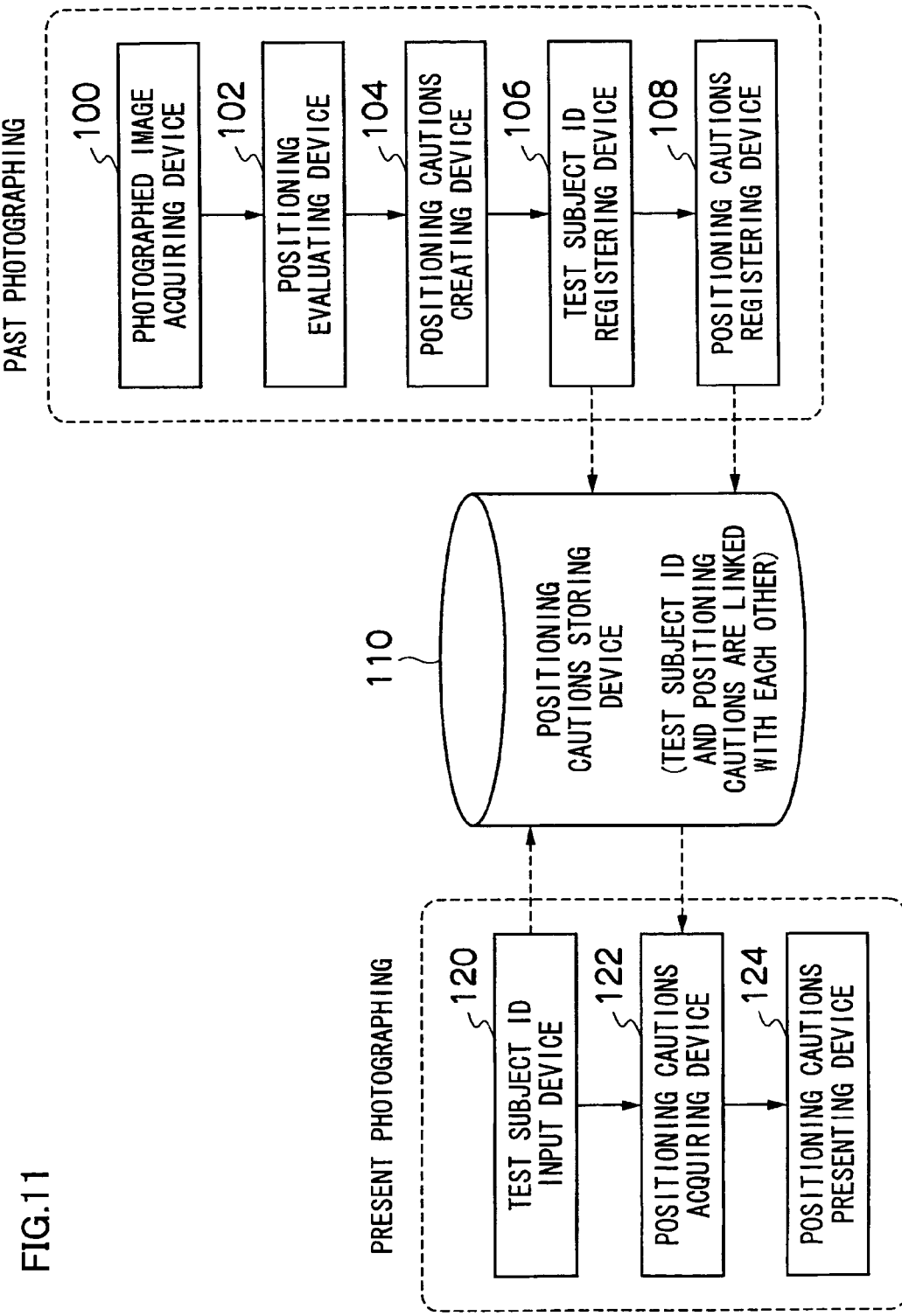
FIG. 11 is a functional block diagram showing a first embodiment of an apparatus for aiding photographing of a medical image according to the present invention.

FIG. 11 is a function block diagram showing a first embodiment of an apparatus for aiding photographing of a medical image according to the present invention.

In FIG. 11, a photographed image acquiring device 100 corresponds to the communication I/F 18 and the like shown in FIG. 1, and takes in a medical image directly through the photographing apparatus 40 and the console 42, or from the image DB 42.

A positioning evaluating device 102 analyzes the medical image which is taken in, extracts an anatomical structure (breast, a mammary gland, a greater pectoral muscle, a nipple and the like) from the medical image, and gives the evaluation points to the respective evaluation items of positioning as described above on the basis of these extracted structures.

A positioning cautions creating device 104 creates positioning cautions based on the evaluation points of the above described respective evaluation items. More specifically, the positioning cautions creating device 104 reads the corresponding positioning cautions from the database in which the evaluation points according to the respective items of positioning and the positioning cautions are linked with each other and stored in advance as described above.

Hereinafter, concrete examples of the evaluation points according to the respective items of positioning and the positioning cautions will be described.

Example 1

When the evaluation points of the space behind the mammary gland is less than two points, the cautions as follows are created.

"The mammary gland cannot be sufficiently visualized. Perform photographing with attention paid to the following points.

(1) Pull the mammary gland sufficiently inward.
(2) Straighten up the body of an examinee.
(3) Do not remove a hand from below when removing the hand after compression."

Example 2

When the evaluation point of the greater pectoral muscle is two points or less, the cautions as described below are created based on the evaluation results of the greater pectoral muscle and extension of the mammary gland.

Pattern 1: when the length to the lower end portion of the greater pectoral muscle from the upper end of the image is shorter than the length to the nipple portion from the upper end of the image, and when the area of the greater pectoral muscle is 10% or less of the area of the entire breast "The greater pectoral muscle is not sufficiently photographed. Perform photographing by pulling the pectoral muscle sufficiently inward."

Pattern 2: when the length to the lower end portion of the greater pectoral muscle from the upper end of the image is longer than the length to the nipple portion from the upper end of the image, or when the area of the greater pectoral muscle is 50% or more of the area of the entire breast, and the extension of the mammary gland is less than two points, "The greater pectoral muscle is excessively photographed, and therefore, compression and extension of the mammary gland are insufficient. In the case of a small breast, photograph the breast by slightly excluding the pectoral muscle."

Pattern 3: when the greater pectoral muscle is photographed in the recessed shape "The grater pectoral muscle is photographed in the recessed shape. Perform photographing with attention being paid to the following points.

(1) Perform photographing by pulling the pectoral muscle sufficiently inward.

(2) The examinee is not likely to be relaxed. Put the arm of the examinee at the rear of the cassette holder by bending the elbow, and allow the hand to hold the handle of the support arm lightly."

Example 3

When the evaluation points of extension of the mammary gland is less than two points, and in the case other than the above described pattern 2, the cautions as described below are created.

"Compression and extension of the mammary gland are insufficient. Make sure to draw the breast and elevate the arm." Further, in the case which is not applied to any of the above described cases, it is determined as suitable positioning and is determined as "no cautions".

The positioning cautions are not limited to the above described example, and various kinds of cautions are prepared in accordance with the evaluation point of the respective evaluation items of positioning and the combination of the respective evaluation items and evaluation points, and suitable positioning cautions are selected for evaluation result of positioning of the medical image which is the evaluation target.

The test subject ID of the test subject corresponding to the medical image which is evaluated as described above and the positioning cautions of the medical image are linked with each other, and are stored in a positioning cautions storing device 110 by a test subject ID registering device 106 and a positioning cautions registering device 108.

The test subject ID registering device 106 includes an input device such as the keyboard 30. When the test subject ID corresponding to the medical image (positioning cautions) is registered by the registering operation by the operator or when the test subject ID is added to the medical image as the accessory information, the test subject ID registering device 106 reads the test subject ID and registers the test subject ID. The positioning cautions storing device 110 corresponds to the hard disk device 20 of FIG. 1.

In this manner, in the positioning cautions storing device 110, the positioning cautions created with respect to the medical images of the respective test subjects which were photographed in the past in the regular checkups or the like and the test subject IDs are stored by being linked with each other.

Here, when a photographer photographs a certain test subject by the photographing aiding apparatus 10, the test subject ID of the test subject is input by a test subject ID input device 120. The test subject ID input device 120 corresponds to the keyboard 30. Alternatively, when the test subject ID is registered due to medical checkup reservation or the like of the test subject in advance, the test subject ID can be input by clicking the registered test subject ID with the mouse 32.

The positioning cautions acquiring device 122 reads the positioning cautions which are registered by being linked with the test subject ID from the positioning cautions storing device 110 when the test subject ID by the test subject ID input device 120 is input.

The positioning cautions acquired by the positioning cautions acquiring device 122 is presented to the photographer by the positioning cautions presenting device 124. The positioning cautions presenting device 124 corresponds to the monitor device 28.

Specifically, when the photographer inputs the test subject ID of the test subject to be photographed, the positioning cautions which is created with respect to the medical image of the test subject which was photographed in the past is read from the positioning cautions storing device 110, and the photographer can confirm the positioning cautions from the positioning cautions presenting device 124. Thereby, the photographer can confirm the positioning cautions due to the physique and the like of the test subject before photographing.

The medical image which is photographed by positioning the test subject after confirming the positioning cautions becomes the photographed image of the past. Therefore, the evaluation points are given to the respective evaluation items of positioning as in the above description. The positioning cautions are created based on the evaluation points of the respective evaluation items, and the created positioning cautions are stored in the positioning cautions storing device 110 by being linked with the test subject ID.

Second Embodiment

Figure 12:
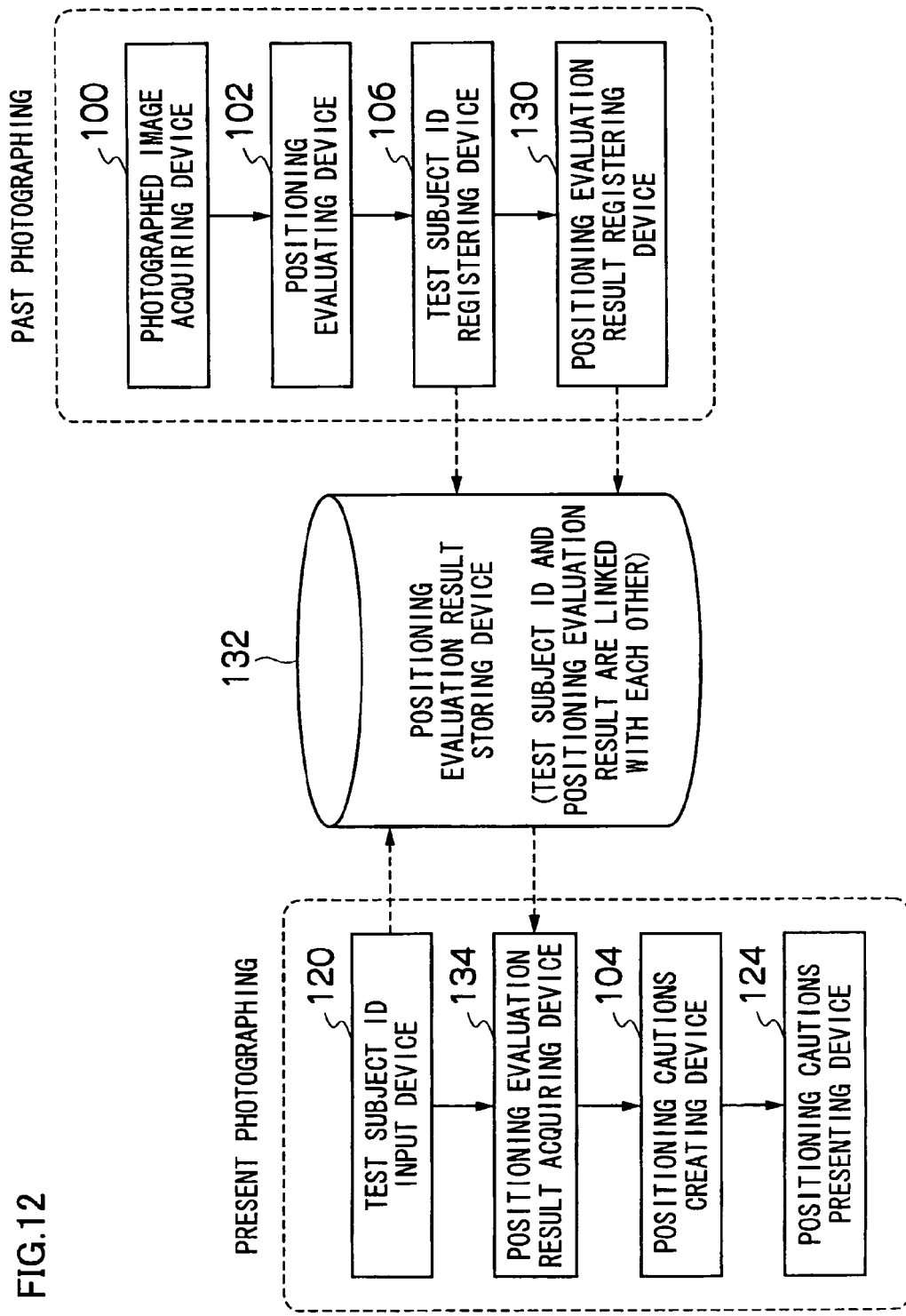
FIG. 12 is a functional block diagram showing a second embodiment of an apparatus for aiding photographing of a medical image according to the present invention.

FIG. 12 is a functional block diagram showing a second embodiment of the apparatus for aiding photographing of a medical image according to the present invention. The parts common to the first embodiment shown in FIG. 11 are assigned with the same reference numerals and characters and the detailed description of them will be omitted.

The second embodiment differs from the aforementioned first embodiment in the point in which the test subject ID and the positioning evaluation result are stored by being linked with each other and the point in which the positioning cautions are created at the time of photographing.

More specifically, the test subject ID of the test subject corresponding to the medical image and the positioning evaluation result evaluated for the medical image by the positioning evaluating device 102 are linked with each other, and stored in a positioning evaluation result storing device 132 by the test subject ID registering device 106 and a positioning evaluation result registering device 130. The positioning evaluation result is the evaluation points according to the respective evaluation items of positioning as shown in FIG. 10.

Here, when the test subject ID of the test subject to be photographed is input by the test subject ID input device 120, a positioning evaluation result acquiring device 134 reads the positioning evaluation result which is stored by being linked with the test subject ID from the positioning evaluation result storing device 132.

The positioning cautions creating device 104 creates the positioning cautions based on the positioning evaluation result acquired by the positioning evaluation result acquiring device 134. The positioning cautions created by the positioning cautions creating device 104 are presented to the photographer by the positioning cautions presenting device 124.

Third Embodiment

Figure 13:
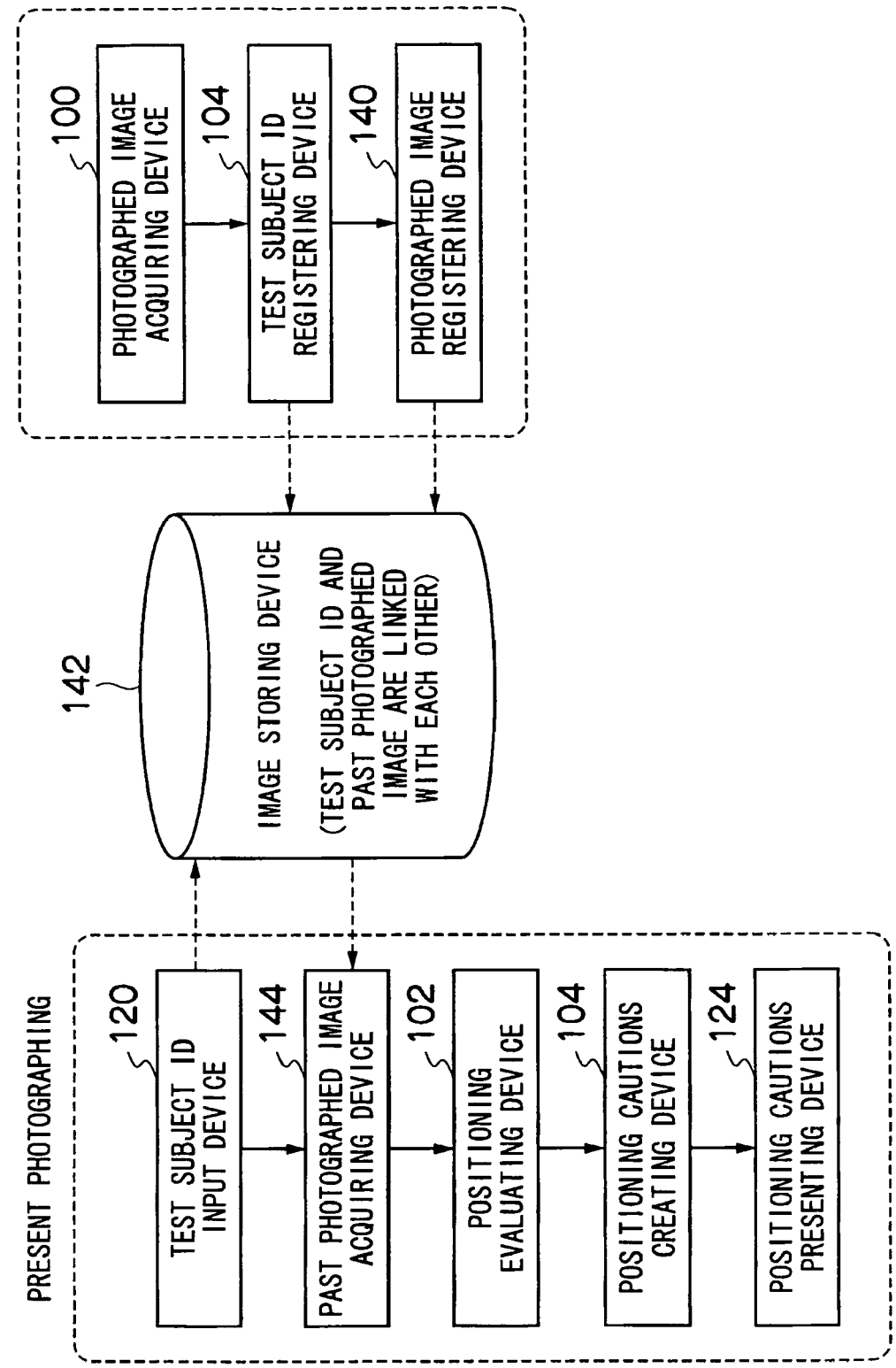
FIG. 13 is a functional block diagram showing a third embodiment of an apparatus for aiding photographing of a medical image according to the present invention.

FIG. 13 is a functional block diagram showing a third embodiment of the apparatus for aiding photographing of a medical image according to the present invention. The parts common to the first embodiment shown in FIG. 11 are assigned with the same reference numerals and characters, and the detailed description of them will be omitted.

The third embodiment differs from the aforementioned first embodiment in the point in which a test subject ID and the photographed image (medical image) of the past are stored by being linked with each other, and the point in which evaluation of positioning is performed for the photographed image of the past and the positioning cautions are created at the time of photographing.

Specifically, the test subject ID of a test subject corresponding to the photographed image and the photographed image are linked with each other, and are stored in an image storing device 142 by the test subject ID registering device 106 and the photographed image registering device 140. The image storing device 142 corresponds to the image DB 44 shown in FIG. 1.

Here, when the test subject ID of the test subject to be photographed is input by the test subject ID input device 120, a past photographed image acquiring device 144 reads the photographed image of the past which is stored by being linked with the test subject ID from the image storing device 142.

The positioning evaluating device 102 analyzes the aforementioned photographed image which is read, extracts the anatomical structures (a breast, a mammary gland, a greater pectoral muscle, a nipple and the like) from the photographed image, and gives the evaluation points to the respective evaluation items of positioning as described above on the basis of these extracted structures.

The positioning cautions creating device 104 creates the positioning cautions based on the evaluation points of the aforementioned evaluation items. The positioning cautions which are created by the positioning cautions creating device 104 are presented to the photographer by the positioning cautions presenting device 124.

Fourth Embodiment

Figure 14:
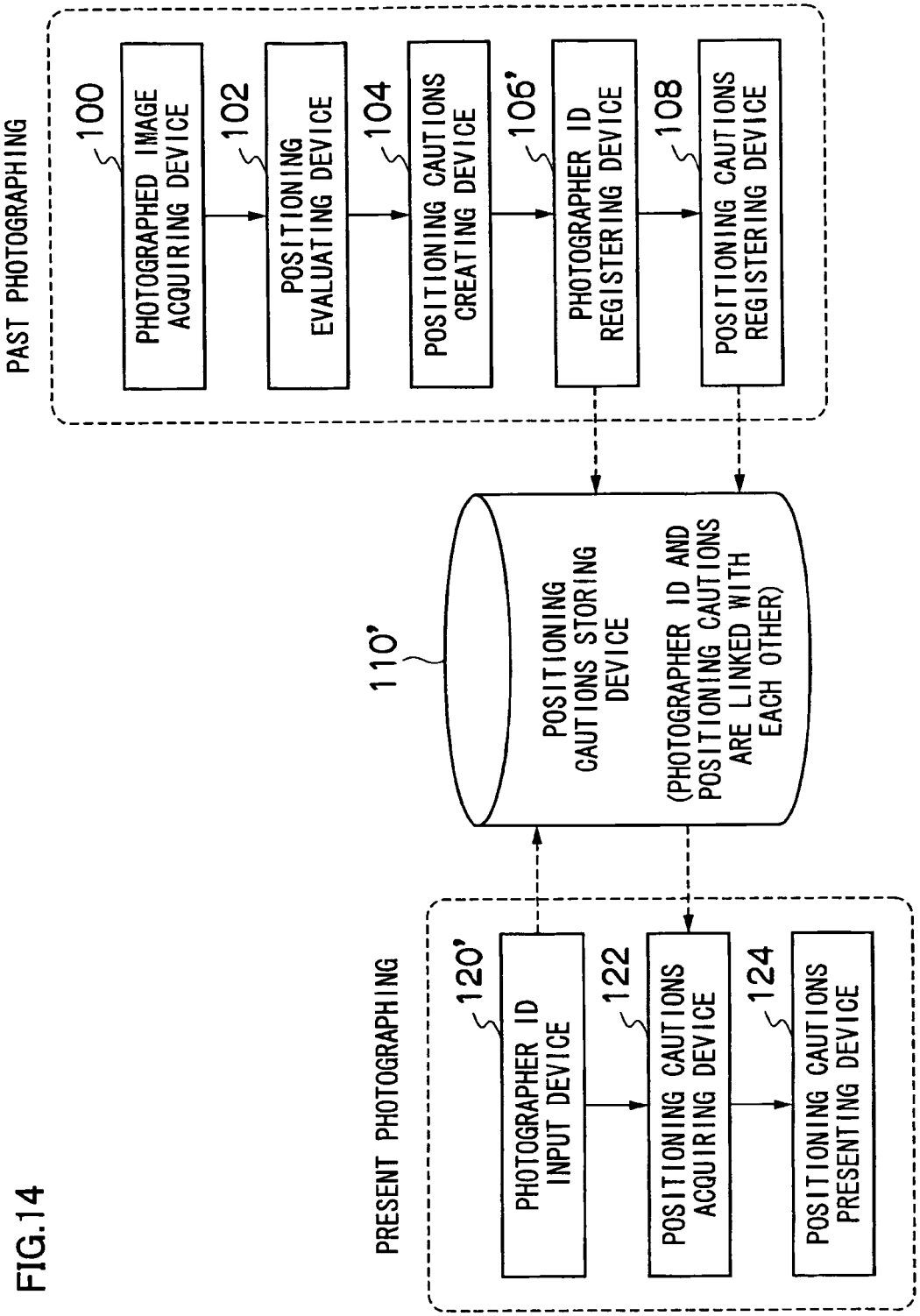
FIG. 14 is a functional block diagram showing a fourth embodiment of an apparatus for aiding photographing of a medical image according to the present invention.

FIG. 14 is a functional block diagram showing a fourth embodiment of the apparatus for aiding photographing of a medical image according to the present invention. The parts common to the first embodiment shown in FIG. 11 are assigned with the same reference numerals and characters, and the detailed description of them will be omitted.

In the first embodiment shown in FIG. 11, the test subject ID and the positioning cautions are linked with each other and stored in the positioning cautions storing device 110, and the corresponding positioning cautions are read by input of the test subject ID. However, the fourth embodiment differs from the first embodiment in the point in which the photographer ID and the positioning cautions are linked with each other and stored in a positioning cautions storing device 110', and the corresponding positioning cautions are read by input of the photographer ID.

Specifically, the photographer ID of the photographer who photographs the medical image and the positioning cautions of the medical image are linked with each other, and stored in the positioning cautions storing device 110' by a photographer ID registering device 106' and a positioning cautions registering device 108.

The photographer ID registering device 106' includes an input device such as the keyboard 30, and registers the photographer ID of the photographer who photographed the medical image by the registering operation by the operator, or reads the photographer ID and registers the photographer ID, when the photographer ID is added to the medical image as the accessory information.

In this manner, the positioning cautions storing device 110' stores the positioning cautions created for the medical image photographed in the past, and the photographer ID of the photographer who photographed the medical image are linked with each other and stored.

When the photographer photographs a certain test subject by the photographing aiding apparatus 10, the photographer inputs the photographer ID (his or her own ID) by a photographer ID input device 120'.

When the photographer ID is input by the photographer ID input device 120', the positioning cautions acquiring device 122 reads the positioning cautions which are linked with the photographer ID and registered from the positioning cautions storing device 110'.

The positioning cautions which are acquired by the positioning cautions acquiring device 122 are presented to the photographer by the positioning cautions presenting device 124. Here, when a plurality of positioning cautions are read, the positioning cautions presenting device 124 presents the positioning cautions which are created for on medical image photographed recently, or a predetermined number of medical images photographed recently.

Thereby, when the photographer inputs his or her own photographer ID, the positioning cautions created with respect to the medical images which were photographed in the past by himself or herself are read from the positioning cautions storing device 110'. The photographer can confirm the positioning cautions from the positioning cautions presenting device 124, and can grasp the points to be improved of his or her own photographing technique and positioning.

Further, the medical image which is photographed by positioning the test subject after confirming the positioning cautions becomes the photographed image of the past. Therefore, the evaluation points are given to the respective evaluation items of positioning as described above, the positioning cautions are created based on the evaluation points of the respective evaluation items, and the created positioning cautions are stored in the positioning cautions storing device 110' by being linked with the photographer ID. Thereby, the photographer can immediately grasp the newest positioning result, and can use the newest positioning result for positioning at the time of the next photographing.

Fifth Embodiment

Figure 15:
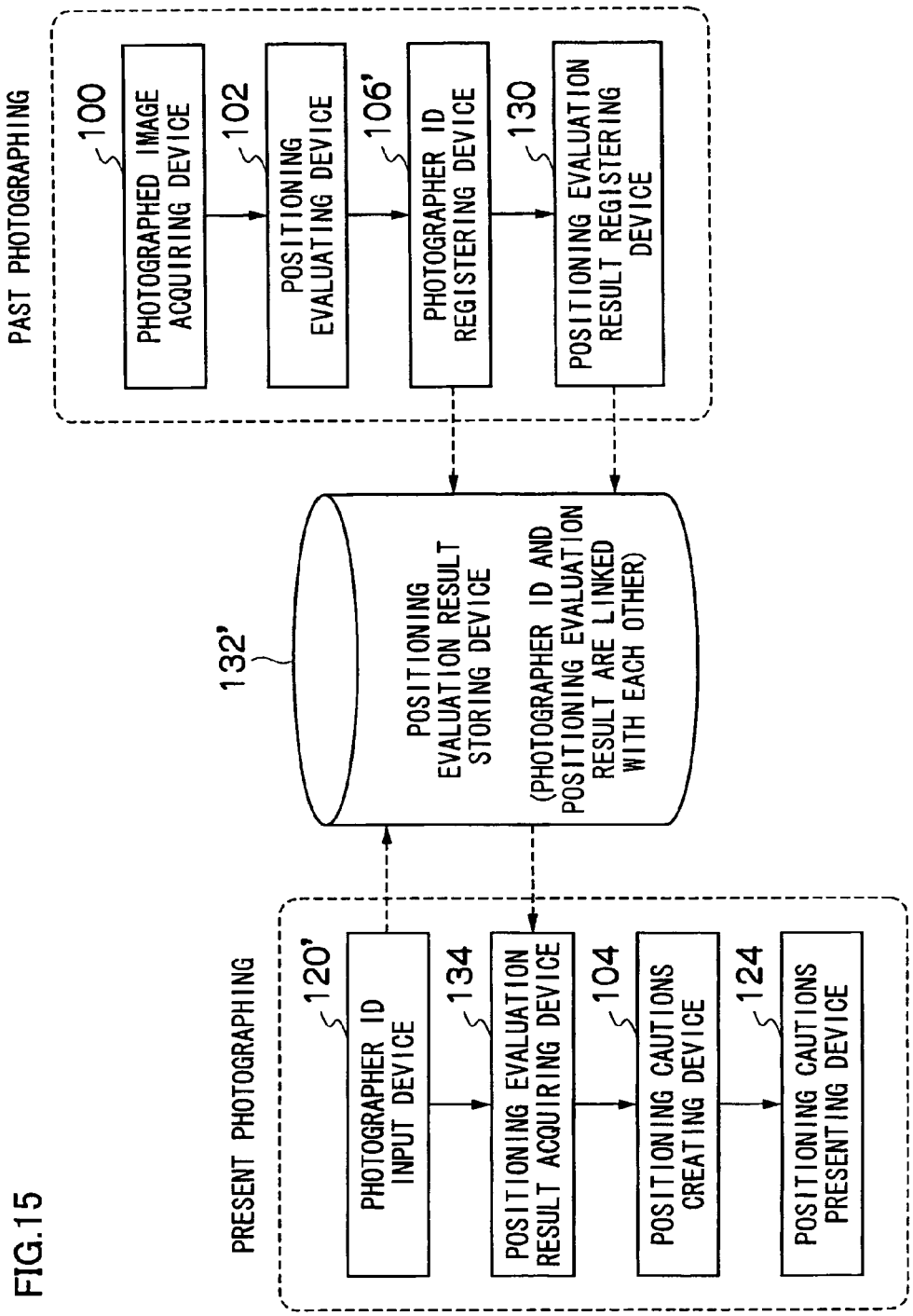
FIG. 15 is a functional block diagram showing a fifth embodiment of an apparatus for aiding photographing of a medical image according to the present invention.

FIG. 15 is a functional block diagram showing a fifth embodiment of the apparatus for aiding photographing of a medical image according to the present invention. The parts common to the second embodiment shown in FIG. 12 are assigned with the same reference numerals and characters, and the detailed description of them will be omitted.

In the second embodiment shown in FIG. 12, the test subject ID and the positioning evaluation result are linked with each other and stored in the positioning evaluation result storing device 132, and the corresponding positioning evaluation result is read by input of the test subject ID. However, the fifth embodiment differs from the second embodiment in the point in which the photographer ID and the positioning evaluation result are linked with each other and stored in a positioning evaluation result storing device 132', and the corresponding positioning evaluation result is read by input of the photographer ID.

Specifically, the photographer ID of the photographer who photographs a medical image and the positioning evaluation result of the medical image are linked with each other, and are stored in the positioning evaluation result storing device 132' by a photographer ID registering device 106' and the positioning evaluation result registering device 130.

The positioning cautions storing device 110' links the positioning evaluation result which is created for the medical image photographed in the past and the photographer ID of the photographer, who photographed the medical image, with each other, and stores them.

When the photographer photographs a certain test subject by the photographing aiding apparatus 10, the photographer inputs the photographer ID (his or her own ID) by the photographer ID input device 120'.

The positioning evaluation result acquiring device 134 reads the positioning evaluation result which is registered by being linked with the photographer ID from the positioning evaluation result storing device 132' when the photographer ID is input by the photographer ID input device 120'.

The positioning cautions creating device 104 creates the positioning cautions based on the positioning evaluation result acquired by the positioning evaluation result acquiring device 134.

The positioning cautions created by the positioning cautions creating device 104 is presented to the photographer by the positioning cautions presenting device 124.

The aforementioned positioning evaluation result acquiring device 134 obtains the average of the acquired positioning evaluation results when acquiring a plurality of positioning evaluation results, and outputs the average positioning evaluation result to the positioning cautions creating device 104. Further, the positioning evaluation result acquiring device 134 does not acquire all the positioning evaluation results for the photographed image (medical image) of the past, but desirably acquires the positioning evaluation results for the medical images which were photographed in the past one month or 50 medical images which were photographed recently, and calculates the average positioning evaluation result to output the average positioning evaluation result to the positioning cautions creating device 104.

Further, the medical image which is photographed by positioning the test subject after confirming the positioning cautions becomes the photographed image of the past. Therefore, the medical image is given the evaluation points for the respective evaluation items of positioning as described above, and the positioning evaluation result is linked with the photographer ID and stored in the positioning evaluation result storing device 132'.

Sixth Embodiment

Figure 16:
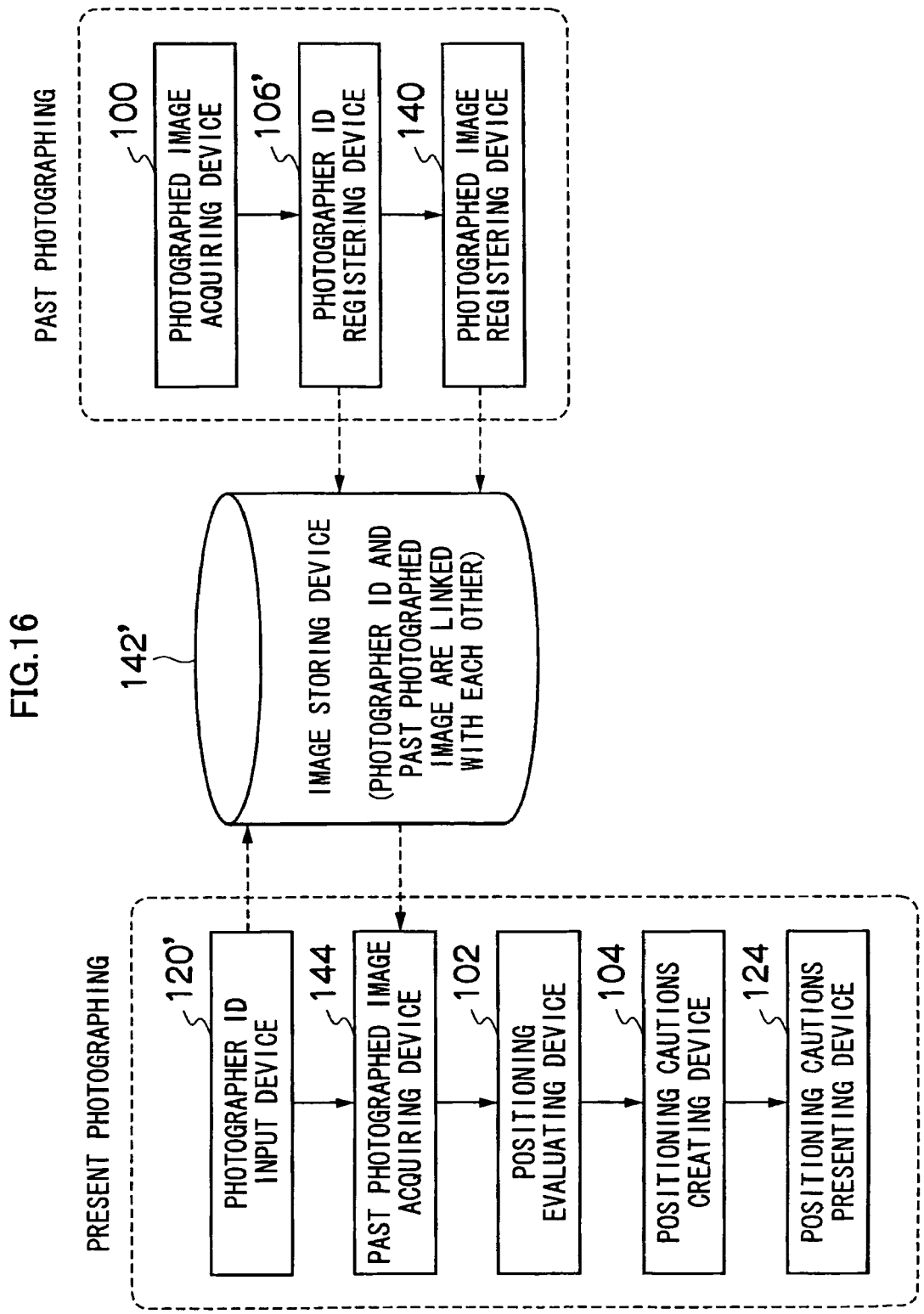
FIG. 16 is a functional block diagram showing a sixth embodiment of an apparatus for aiding photographing of a medical image according to the present invention.

FIG. 16 is a functional block diagram showing a sixth embodiment of the apparatus for aiding photographing of a medical image according to the present invention. The parts common to the third embodiment shown in FIG. 13 are assigned with the same reference numerals and characters, and the detailed description of them will be omitted.

In the third embodiment shown in FIG. 13, the test subject ID and the photographed image (medical image) of the past are linked with each other and stored in the image storing device 142, and the corresponding photographed image is read from input of the test subject ID. The sixth embodiment differs from the third embodiment in the point in which the photographer ID and the photographed image of the past are linked with each other and stored in an image storing device 142', and the corresponding photographed image of the past is read by input of the photographer ID.

Specifically, the photographer ID of the photographer who photographed a medical image, and the medical image is linked with each other, and stored in the image storing device 142' by the photographer ID registering device 106' and the photographed image registering device 140.

When the photographer photographs a certain test subject by the photographing aiding apparatus 10, the photographer inputs the photographer ID (his or her own ID) by the photographer ID input device 120'.

When the photographer ID is input by the photographer ID input device 120', the past photographed image acquiring device 144 reads the photographed image of the past which is stored by being linked with the photographer ID from the image storing device 142'. The past photographed image acquiring device 144 does not acquire all the past photographed images, but desirably acquires the medical images which were photographed in the past one month or 50 medical images which were photographed recently.

The positioning evaluating device 102 analyzes the aforementioned acquired past photographed image (medical image), extracts the anatomical structures (the breast, the mammary gland, the greater pectoral muscle, the nipple and the like) from the medical image, and gives evaluation points to the respective evaluation items of positioning with these extracted structures as the references. When the past photographed image acquiring device 144 acquires a plurality of photographed images, the positioning evaluating device 102 calculates the average positioning evaluation result of the respective photographed images.

The positioning cautions creating device 104 creates the positioning cautions based on the positioning evaluation result calculated by the positioning evaluating device 102. The positioning cautions created by the positioning cautions creating device 104 are presented to the photographer by the positioning cautions presenting device 124.

Modified Example

In each of the above described first embodiment to sixth embodiment, the test subject ID or the photographer ID is input, and the positioning cautions corresponding to the input test subject ID or the photographer ID are presented, but the present invention is not limited to this. The test subject ID and the photographer ID may be input, and the positioning cautions corresponding to the test subject ID and the photographer ID may be presented.

Further, the positioning cautions presented to the monitor device 28 of the photographing aiding apparatus 10 of a medical image may be confirmed by inputting required information from the console 42 of the photographing apparatus 40, the other terminals connected to the network 50 and the like.

The present invention can be also applied to medical images of the other parts without being limited to the breast image. The positioning cautions may be created and presented based on the positioning evaluation result (lung field area, respective inclinations of the left and right lung field regions and the like) of the chest image as shown in, for example, Japanese Patent Application Laid-Open No. 2007-105264.

Further, the present invention is not limited to the above examples, and it goes without saying that various improvements and modifications may be made within the range without departing from the spirit of the present invention.

What is claimed is:

1. An apparatus for aiding photographing of a medical image, comprising:
   an image acquiring device configured to acquire a medical image obtained by radiation-photographing of a part including a diagnosis target region of a test subject;
   a positioning evaluating device configured to analyze the acquired medical image and evaluate positioning of the test subject at a time of the radiation-photographing;
   a positioning cautions creating device configured to create positioning cautions based on an evaluation result by the positioning evaluating device;
   a positioning cautions presenting device configured to present the positioning cautions created by the positioning cautions creating device;

a positioning cautions storing device configured to store test subject identification information for identifying the test subject corresponding to the medical image and positioning cautions created for the medical image by the positioning cautions creating device by linking the test subject identification information and the positioning cautions with each other; and a test subject identification information input device configured to input the test subject identification information, wherein when the test subject identification information of the test subject to be photographed is input by the test subject identification information input device, the positioning cautions presenting device reads the positioning cautions stored by being linked with the input test subject identification information from the positioning cautions storing device, and presents the read positioning cautions.

2. The apparatus for aiding photographing of the medical image according to claim 1,
wherein the positioning evaluating device makes evaluation for each of a plurality of items of the positioning, and outputs an evaluation result of each of the items.

3. The apparatus for aiding photographing of the medical image according to claim 1, further comprising:
an image storing device configured to store the medical image and test subject identification information for identifying the test subject corresponding to the medical image by linking the medical image and the test subject identification information with each other; and
a test subject identification information input device configured to input the test subject identification information,
wherein when the test subject identification information of the test subject to be photographed is input by the test subject identification information input device, the image acquiring device acquires the medical image stored by being linked with the input test subject identification information from the image storing device.

4. The apparatus for aiding photographing of the medical image according to claim 3, further comprising:
a photographer identification information input device configured to input a photographer identification information for identifying a photographer who photographed the medical image,
wherein the image storing device for stores the medical image and the photographer identification information by linking the medical image and the photographer identification information with each other, and
wherein when the photographer identification information is input by the photographer identification information input device, the image acquiring device acquires the medical image corresponding to the input photographer identification information from the image storing device.

5. The apparatus for aiding photographing of the medical image according to claim 1, further comprising:
a photographer identification information input device configured to input a photographer identification information for identifying a photographer who photographed the medical image,
wherein the positioning cautions storing device stores the photographer identification information, and the positioning cautions created for the medical image by the positioning cautions creating device by linking the photographer identification information and the positioning cautions with each other, and wherein when the photographer identification information is input by the photographer identification information input device, the positioning cautions presenting device reads the positioning cautions stored by being linked with the input photographer identification information from the positioning cautions storing device, and presents the read positioning cautions.

6. The apparatus for aiding photographing of the medical image according to claim 1, further comprising:
an image storing device configured to store the medical image and photographer identification information for identifying a photographer who photographed the medical image by linking the medical image and the photographer identification information with each other; and
a photographer identification information input device configured to input the photographer identification information,
wherein when the photographer identification information is input by the photographer identification information input device, the image acquiring device acquires the medical image corresponding to the input photographer identification information from the image storing device.

7. The apparatus for aiding photographing of the medical image according to claim 1,
wherein the positioning evaluating device comprises a structure extracting device configured to extract an anatomical structure from the acquired medical image, and evaluates whether the medical image is photographed by being properly positioned on the basis of the extracted structure.

8. The apparatus for aiding photographing of the medical image according to claim 7,
wherein the medical image is a breast image photographed by a mammography apparatus, and
the structure extracting device extracts at least a breast, a mammary gland, a greater pectoral muscle and a nipple as the extracted structure.

9. The apparatus for aiding photographing of the medical image according to claim 8,
wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image.

10. The apparatus for aiding photographing of the medical image according to claim 9,
wherein the positioning evaluating device evaluates the symmetry respectively based on an area ratio of left and right breasts, an area ratio of left and right mammary glands, and an area ratio of left and right greater pectoral muscles which are extracted from the breast image, and the positioning evaluating device makes an evaluation with respect to the first positioning evaluation item based on evaluation result of the symmetry.

11. The apparatus for aiding photographing of the medical image according to claim 9,
wherein the positioning evaluating device makes evaluation with respect to the second positioning evaluation item based on whether or not the left and right nipples can be extracted from the breast images.

12. The apparatus for aiding photographing of the medical image according to claim 9,
wherein the positioning evaluating device makes evaluation with respect to the third positioning evaluation item based on a lower end position of the greater pectoral muscle extracted from the breast image, a shape of the greater pectoral muscle, and an area ratio of the greater pectoral muscle to the breast.

13. The apparatus for aiding photographing of the medical image according to claim 9,
wherein the positioning evaluating device makes evaluation with respect to the fourth positioning evaluation item based on a length of a line composed of a boundary of the greater pectoral muscle extracted from the breast image and an image end at a side of a chest wall, and a length of the mammary gland extracted from the breast image which overlaps the line.

14. The apparatus for aiding photographing of the medical image according to claim 9,
wherein the positioning evaluating device comprises a detecting device configured to detect a skin line of the breast image, and makes evaluation with respect to the fifth positioning evaluation item based on the shape of the detected skin line.

15. The apparatus for aiding photographing of the medical image according to claim 9,
wherein the positioning evaluating device comprises a calculating device configured to calculate a contrast value in the mammary gland of the mammary gland extracted from the breast image, and makes evaluation with respect to the sixth positioning evaluation item based on an area ratio of the breast and the mammary gland except for the greater pectoral muscle extracted from the breast image, and the calculated contrast value in the mammary gland.

16. An apparatus for aiding photographing of a medical image, comprising:
an image acquiring device configured to acquire a medical image obtained by radiation-photographing of a part including a diagnosis target region of a test subject;
a positioning evaluating device configured to analyze the acquired medical image and evaluate positioning of the test subject at a time of the radiation-photographing;
an evaluation result storing device configured to store test subject identification information for identifying the test subject corresponding to the medical image and the evaluation result evaluated for the medical image by the positioning evaluating device by linking the test subject identification information and the evaluation result with each other; and
a test subject identification information input device configured to input the test subject identification information,
wherein when the test subject identification information of the test subject to be photographed is input by the test subject identification information input device, the apparatus reads the evaluation result stored by being linked with the input test subject identification information from the evaluation result storing device, creates positioning cautions based on the read evaluation result, and presents the positioning cautions.

17. The apparatus for aiding photographing of the medical image according to claim 16, further comprising:
a photographer identification information input device configured to input a photographer identification information for identifying a photographer who photographed the medical image,
wherein the evaluation result storing device stores the photographer identification information, and the evaluation result evaluated for the medical image by the positioning evaluating device by linking the photographer identification information and the evaluation result with each other, and
wherein when the photographer identification information is input by the photographer identification information input device, the apparatus reads the evaluation result stored by being linked with the input photographer identification information from the evaluation result storing device, creates positioning cautions based on the read evaluation result, and presents the positioning cautions.

18. The apparatus for aiding photographing of the medical image according to claim 16, further comprising:
a positioning cautions creating device configured to create positioning cautions based on an evaluation result by the positioning evaluating device; and
a positioning cautions presenting device configured to present the positioning cautions created by the positioning cautions creating device.

19. The apparatus for aiding photographing of the medical image according to claim 18, further comprising:
a photographer identification information input device configured to input a photographer identification information for identifying a photographer who photographed the medical image,
wherein the evaluation result storing device stores the photographer identification information, and the evaluation result evaluated for the medical image by the positioning evaluating device by linking the photographer identification information and the evaluation result with each other, and
wherein when the photographer identification information is input by the photographer identification information input device, the positioning cautions creating device reads the evaluation result stored by being linked with the input photographer identification information from the evaluation result storing device, and creates the positioning cautions based on the read evaluation result.

20. The apparatus for aiding photographing of the medical image according to claim 16,
wherein the positioning evaluating device comprises a structure extracting device configured to extract an anatomical structure from the acquired medical image, and evaluates whether the medical image is photographed by being properly positioned on the basis of the extracted structure.

21. The apparatus for aiding photographing of the medical image according to claim 20,
wherein the medical image is a breast image photographed by a mammography apparatus, and
the structure extracting device extracts at least a breast, a mammary gland, a greater pectoral muscle and a nipple as the extracted structure.

22. An apparatus for aiding photographing of a medical image, comprising:
an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

a positioning cautions creating device configured to create positioning cautions based on an evaluation result by the positioning evaluating device;

a positioning cautions presenting device configured to present the positioning cautions created by the positioning cautions creating device;

a positioning cautions storing device configured to store photographer identification information for identifying a photographer who photographed the medical image, and positioning cautions created for the medical image by the positioning cautions creating device by linking the photographer identification information and the positioning cautions with each other; and a photographer identification information input device configured to input the photographer identification information, wherein when the photographer identification information is input by the photographer identification information input device, the positioning cautions presenting device reads the positioning cautions stored by being linked with the input photographer identification information from the positioning cautions storing device, and presents the read positioning cautions.

23. The apparatus for aiding photographing of the medical image according to claim 22, wherein the positioning evaluating device comprises a structure extracting device configured to extract an anatomical structure from the acquired medical image, and evaluates whether the medical image is photographed by being properly positioned on the basis of the extracted structure.

24. The apparatus for aiding photographing of the medical image according to claim 23, wherein the medical image is a breast image photographed by a mammography apparatus, and the structure extracting device extracts at least a breast, a mammary gland, a greater pectoral muscle and a nipple as the extracted structure.

25. An apparatus for aiding photographing of a medical image, comprising:

an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

an evaluation result storing device configured to store photographer identification information for identifying a photographer who photographed the medical image, and evaluation result evaluated for the medical image by the positioning evaluating device by linking the photographer identification information and the evaluation result with each other; and a photographer identification information input device configured to input the photographer identification information, wherein when the photographer identification information is input by the photographer identification information input device, the apparatus reads the evaluation result stored by being linked with the input photographer identification information from the evaluation result storing device, creates positioning cautions based on the read evaluation result, and presents the positioning cautions.

26. The apparatus for aiding photographing of the medical image according to claim 25, further comprising:

a positioning cautions creating device configured to create positioning cautions based on an evaluation result by the positioning evaluating device; and a positioning cautions presenting device configured to present the positioning cautions created by the positioning cautions creating device.

27. The apparatus for aiding photographing of the medical image according to claim 25, wherein the positioning evaluating device comprises a structure extracting device configured to extract an anatomical structure from the acquired medical image, and evaluates whether the medical image is photographed by being properly positioned on the basis of the extracted structure.

28. The apparatus for aiding photographing of the medical image according to claim 27, wherein the medical image is a breast image photographed by a mammography apparatus, and the structure extracting device extracts at least a breast, a mammary gland, a greater pectoral muscle and a nipple as the extracted structure.

29. A non-transitory computer readable recording medium for aiding photographing of a medical image, the computer readable recording medium having computer readable program code embodied therein, the computer readable program code comprising:

a computer-readable program code for causing a computer to acquire a medical image obtained by radiation-photographing a part including a diagnosis target part of a test subject;

a computer-readable program code for causing a computer to analyze the acquired medical image and to evaluate positioning of the test subject at a time of the radiation-photographing;

a computer-readable program code for causing a computer to store test subject identification information for identifying the test subject corresponding to the medical image and the evaluation result evaluated for the medical image by linking the test subject identification information and the evaluation result with each other; and a computer-readable program code for causing a computer to input the test subject identification information, wherein when the test subject identification information of the test subject to be photographed is input, the evaluation result stored by being linked with the input test subject identification information is read, and positioning cautions are created based on the read evaluation result.

30. An apparatus for aiding photographing of a medical image, comprising:

an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

a positioning cautions creating device configured to create positioning cautions based on an evaluation result by the positioning evaluating device; and a positioning cautions presenting device configured to present the positioning cautions created by the positioning cautions creating device;

wherein the positioning evaluating device comprises a structure extracting configured to extract an anatomical structure from the acquired medical image, and evaluates whether the medical image is photographed by being properly positioned on the basis of the extracted structure, wherein the medical image is a breast image photographed by a mammography apparatus, wherein the structure extracting device extracts at least a breast, a mammary gland, a greater pectoral muscle and a nipple as the extracted structure, wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and wherein the positioning evaluating device evaluates the symmetry respectively based on an area ratio of left and right breasts, an area ratio of left and right mammary glands, and an area ratio of left and right greater pectoral muscles which are extracted from the breast image, and the positioning evaluating device makes an evaluation with respect to the first positioning evaluation item based on evaluation result of the symmetry.

31. An apparatus for aiding photographing of a medical image, comprising:

an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

a positioning cautions creating device configured to create positioning cautions based on an evaluation result by the positioning evaluating device; and a positioning cautions presenting device configured to present the positioning cautions created by the positioning cautions creating device;

wherein the positioning evaluating device comprises a structure extracting device configured to extract an anatomical structure from the acquired medical image, and evaluates whether the medical image is photographed by being properly positioned on the basis of the extracted structure, wherein the medical image is a breast image photographed by a mammography apparatus, wherein the structure extracting device extracts at least a breast, a mammary gland, a greater pectoral muscle and a nipple as the extracted structure, wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and wherein the positioning evaluating device makes evaluation with respect to the second positioning evaluation item based on whether or not the left and right nipples can be extracted from the breast images.

32. An apparatus for aiding photographing of a medical image, comprising:

an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

a positioning cautions creating device configured to create positioning cautions based on an evaluation result by the positioning evaluating device; and a positioning cautions presenting device configured to present the positioning cautions created by the positioning cautions creating device;

wherein the positioning evaluating device comprises a structure extracting device configured to extract an anatomical structure from the acquired medical image, and evaluates whether the medical image is photographed by being properly positioned on the basis of the extracted structure, wherein the medical image is a breast image photographed by a mammography apparatus, wherein the structure extracting device extracts at least a breast, a mammary gland, a greater pectoral muscle and a nipple as the extracted structure, wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and wherein the positioning evaluating device makes evaluation with respect to the third positioning evaluation item based on a lower end position of the greater pectoral muscle extracted from the breast image, a shape of the greater pectoral muscle, and an area ratio of the greater pectoral muscle to the breast.

33. An apparatus for aiding photographing of a medical image, comprising:

an image acquiring device configured to acquire a medical image obtained by radiation-photographing of a part including a diagnosis target region of a test subject;

a positioning evaluating device configured to analyze the acquired medical image and evaluate positioning of the test subject at a time of the radiation-photographing;

a positioning cautions creating device configured to create positioning cautions based on an evaluation result by the positioning evaluating device; and a positioning cautions presenting device configured to present the positioning cautions created by the positioning cautions creating device;

wherein the positioning evaluating device comprises a structure extracting device configured to extract an anatomical structure from the acquired medical image, and evaluates whether the medical image is photographed by being properly positioned on the basis of the extracted structure, wherein the medical image is a breast image photographed by a mammography apparatus, wherein the structure extracting device extracts at least a breast, a mammary gland, a greater pectoral muscle and a nipple as the extracted structure, wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and wherein the positioning evaluating device makes evaluation with respect to the fourth positioning evaluation item based on a length of a line composed of a boundary of the greater pectoral muscle extracted from the breast image and an image end at a side of a chest wall, and a length of the mammary gland extracted from the breast image which overlaps the line.

34. An apparatus for aiding photographing of a medical image, comprising:
- an image acquiring device configured to acquire a medical image obtained by radiation-photographing of a part including a diagnosis target region of a test subject;
- a positioning evaluating device configured analyze the acquired medical image and evaluate positioning of the test subject at a time of the radiation-photographing;
- a positioning cautions creating device configured to create positioning cautions based on an evaluation result by the positioning evaluating device; and
- a positioning cautions presenting device configured to present the positioning cautions created by the positioning cautions creating device;
- wherein the positioning evaluating device comprises a structure extracting device configured to extract an anatomical structure from the acquired medical image, and evaluates whether the medical image is photographed by being properly positioned on the basis of the extracted structure,
- wherein the medical image is a breast image photographed by a mammography apparatus,
- wherein the structure extracting device extracts at least a breast, a mammary gland, a greater pectoral muscle and a nipple as the extracted structure,
- wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and
- wherein the positioning evaluating device comprises a detecting device configured to detect a skin line of the breast image, and makes evaluation with respect to the fifth positioning evaluation item based on the shape of the detected skin line.

35. An apparatus for aiding photographing of a medical image, comprising:
- an image acquiring device configured to acquire a medical image obtained by radiation-photographing of a part including a diagnosis target region of a test subject;
- a positioning evaluating device configured to analyze the acquired medical image and evaluate positioning of the test subject at a time of the radiation-photographing;
- a positioning cautions creating device configured to create positioning cautions based on an evaluation result by the positioning evaluating device; and
- a positioning cautions presenting device configured to present the positioning cautions created by the positioning cautions creating device;
- wherein the positioning evaluating device comprises a structure extracting device configured to extract an anatomical structure from the acquired medical image, and evaluates whether the medical image is photographed by being properly positioned on the basis of the extracted structure,
- wherein the medical image is a breast image photographed by a mammography apparatus,
- wherein the structure extracting device extracts at least a breast, a mammary gland, a greater pectoral muscle and a nipple as the extracted structure,
- wherein the positioning evaluating device makes evaluation with respect to at least two evaluation items out of a first positioning evaluation item relating to lateral symmetry of the breast images, a second positioning evaluation item relating to visualization of the nipple in the breast image, a third positioning evaluation item relating to visualization of the greater pectoral muscle in the breast image, a fourth positioning evaluation item relating to visualization of fat tissue behind the mammary gland in the breast image, a fifth positioning evaluation item relating to visualization of abdominal tissue under the breast in the breast image, and a sixth positioning evaluation item relating to extension of the mammary gland in the breast image, and
- wherein the positioning evaluating device comprises a calculating device configured to calculate a contrast value in the mammary gland of the mammary gland extracted from the breast image, and makes evaluation with respect to the sixth positioning evaluation item based on an area ratio of the breast and the mammary gland except for the greater pectoral muscle extracted from the breast image, and the calculated contrast value in the mammary gland.

* * * * *